United States Patent [19]

Little, II

[11] Patent Number: 5,639,727

[45] Date of Patent: Jun. 17, 1997

[54] THERAPEUTIC USES OF BACTERICIDAL/ PERMEABILITY INCREASING PROTEIN PRODUCTS

[75] Inventor: Roger G. Little, II, Benicia, Calif.

[73] Assignee: XOMA Corporation, Berkeley, Calif.

[21] Appl. No.: 415,158

[22] Filed: Mar. 31, 1995

Related U.S. Application Data

[63] Continuation of Ser. No. 93,202, Jul. 15, 1993, abandoned, which is a continuation-in-part of Ser. No. 30,644, Mar. 12, 1993, Pat. No. 5,348,942.

[51] Int. Cl.$^6$ .................... A61K 38/00; C12P 21/06; C07K 1/00; C07K 2/00
[52] U.S. Cl. .................... 514/12; 514/13; 514/14; 514/15; 514/21; 435/69.1; 530/324; 530/350
[58] Field of Search ........................ 514/12, 13, 14, 514/15, 21; 530/350, 324; 435/69.1

[56] References Cited

U.S. PATENT DOCUMENTS

| | | | |
|---|---|---|---|
| 5,086,164 | 2/1992 | Maione et al. | 530/324 |
| 5,112,946 | 5/1992 | Maione | 530/324 |
| 5,171,739 | 12/1992 | Scott et al. | 514/12 |
| 5,357,041 | 10/1994 | Roberts et al. | 530/326 |
| 5,491,130 | 2/1996 | Roberts et al. | 514/13 |

FOREIGN PATENT DOCUMENTS

| | | |
|---|---|---|
| WO92/01003 | 1/1992 | WIPO . |
| WO92/02240 | 2/1992 | WIPO . |
| WO92/03535 | 3/1992 | WIPO . |
| WO93/13794 | 7/1993 | WIPO . |

OTHER PUBLICATIONS

Dialog Abstract File 155 Accesion No. 92257868, Kaklamanis, 1992. Clin Rheumatol. 11(1):41–47.

Reclini et al. 1988. (Abstract: Dialog File 155 Accession No. 88326267) Biochem. J. 252(2):515–519.

Murav'ev, 1980. (Abstract: Biosis No.: 73034154) Ter Arkh 52(11):126–129.

Marra et al. Aug. 23, 1990. (Abstract; WPI Accession No.: 90–274947/36.

Azizkhan et al., "Mast Cell Heparin Stimulates Migration of Capillary Endothelial Cells In Vitro," *J. Exp. Med.*, 152:931–944 (Oct. 1980).

Brahn, "Animal Modles of Rheumatoid Arthritis," *Clin. Orthopaedics and Related Res.*, 265:42–53 (Apr. 1991).

Castellot et al., "Heparin Potentiation of 3T3–Adipocyte Stimulated Angiogenesis: Mechanism of Action on Endothelial Cells," *J. Cell. Phys.*127:328–329 (1986).

Cremer et al., "Collagen–Induced Arthritis In Rats," *J. Immunol.*, 149(3):1045–1053 (Aug. 1, 1992).

Folkman et al., "Angiogenesis Inhibition and Tumor Regression Caused by Heparin or a Heparin Fragment in the Presence of Cortisone," *Science*, 221:719–725 (Aug. 19, 1983).

Gallagher, "Heparan Sulphates as Membrane Receptors for the Fibroblast Growth Factors," *Eur. J. Clin. Chem. Clin. Biochem.*, 32(4):239–247 (1994).

Harris, "Rheumatoid Arthritis Pathology and Implications for Therapy," *New Engl. J. Med.*, 322(18):1277–1289 (1990).

Ishihara et al., "A Cell Based Assay for Evaluating the Interaction of Heparin–like Molecules and Basic Fibroblast," *Analytical Biochem.*, 202:310–315 (1992).

Kingsley and Sieper, "Current perspectives in reactive arthritis," *Immunol. Today*, 14(8):387–391 (1993).

Leff, "NCI Seeks Company To Co–Develop Anti–Cancer Drugs That Block Tumor Angiogenesis," *BioWorld Today*, 7(125):1&5 (Jun. 26, 1996).

Lichtman et al., "Reactivation of Arthritis Induced by Small Bowel Bacterial Overgrowth in Rats: Role of Cytokines, Bacteria, and Bacterial Polymers," *Infect. Immun.*, 63(6):2295–2301 (Jun. 1995).

Mitchell and Wilks, "Inhibitors of Angiogenesis", Chapter 15, pp. 139–148 in *Annual Reports in Medical Chemistry*, vol. 27, Academic Press, Inc. (1992).

Murav'ev et al., "Effect of Heparin Therapy on Clinico–Laboratory Indicators In Rheumatoid Arthritis Patients," *Ter. Arkh.*, 52(11);126–129 (1980)—English translation.

Phadke et al., "Evaluation of the Effects of Various Anti–Arthritic Drugs on Type II Collagen–Induced Mouse Arthritis Model," *Immunopharmacology*, 10:51–60 (1985).

Stuart et al., "Nature and the Specificity of the Immune Response to Collagen in Type II Collagen–induced Arthritis in Mice", *J. Clin. Invest.*, 69:673–683 (Mar. 1982).

Vogel et al., "Modulation of Endothelial Cell Proliferation, Adhesion, and Motility by Recombinant Heparin–Binding Domain and Synthetic Peptides From the Type I Repeats of Thrombospondin", *J. Cellular Biochem.*, 53:74–84 (1993).

Weiss et al., "Determinants of the Action of Phospholipases A on the Envelope Phospholipids of *Escherichia coli,*" *J. Biol. Chem.*, 254(21):11010–11014 (1979).

Wooley, "Animal models of rheumatoid arthritis," *Curr. Opp. Rheumat.*, 3:407–420 (1991).

Yayon et al., "Cell Surface, Heparin–Like Molecules are Required for Binding of Basic Fibroblast Growth Factor to Its High Affinity Receptor", *Cell*, 64:841–848 (Feb. 22, 1991).

Charles, et al., *J. Biol. Chem.*, "The Three–dimensional Structure of Bovine Platelet Factor 4 at 3.0 A Resolution," 264(4):29092–2099 (Feb. 5, 1989).

Cook, et al., *Circulation*, "Platelet Factor 4 Efficiently Reverses Heparin Anticoagulation in the Rat Without Adverse Effects of Heparin–Protamine Complexes," 85(3): 1102–1109 (Mar., 1992).

Elsbach, et al., *Inflammation: Basic Principles and Correlates*, "Oxygen–Independent Antimicrobial Systems of Phagocytes," 2nd. Ed., Review Press, Ltd. Chapter 30, pp. 603–636 (1992).

Elsbach, et al., *J. Biol. Chem.*, "Separation and Purification of a Potent Bactericidal/Permeability–increasing Protein and a closely Associated Phospholipase A$_2$ from Rabbit Polymorphonuclear Leukocytes," 254(21): 11000–11009 (Nov. 10, 1979).

Folkman, et al., *Inflammation: Basic Principles and Correlates*, "Abiogenesis and Inflammation," 2nd, Ed., Review Press, Ltd., Chapter 40, pp. 821–839 (1992).

Gammon, et al., *J. Exp. Med.*, "T Cell Determinant Structure: Cores and Determinant Envelopes in Three Major Mouse Hsitocompatability Complex Halotypes," 173:609–617 (Mar., 1991).

Garcia, et al., *BioWorld Today*, "Repligen IND for Platelet Factor," p. 5 (Jan. 11, 1983).

Gazzano–Santoro, et al., *Infect. Immunol.*, "High Affinity Binding of the Bactericidal/Permeability Increasing Protein and a Recombinant Amino–Terminal Fragment to the Lipid A Region of Lipopolysacchride," 60(11): 4754–4761 (Nov., 1992).

Gray, et al., *J. Biol. Chem.*, "Cloning of the cDNA of a Human Neutrophil Bactericidal Protein," 264(16): 9505–9509 (Jun. 5, 1989).

Heyderman, et al., *Thrombosis Res.*, "Reduction of the Anticoagulant Activity of Glycosaminoglycans on the Surface of the Vascular Endothelium by Endotoxin and Neutrophils: Evaluation by an Amidolytic Assay," 67: 677–685 (Apr. 28, 1992).

Hiti–Harper, et al., *Science*, "Platelet Factor 4: An Inhibitor of Collagenase," 199: 991–992 (Mar. 3, 1978).

Maeji, et al. *J. Immunol. Methods*, "Multi–pin Peptide Strategy for T cell determinant analysis," 134: 23–33 (1990).

Maione, et al., *Cancer Res.*, "Inhibition of Tumor Growth in Mice by an Analogue of Platelet Factor 4 That Lacks Affinity for Heparin and Retains Potent Angiostatic Activity," 51:2077–2083 (Apr. 15, 1991).

Maione, et al., *CAS BioTech Updates—Antibody Conjugates*, pp. 1, 1334, 117:226303x (Issue Jun. 16, 1992).

Marra, et al., *J. Immunol.*, "The Role of Bactericidal/Permeability–Increasing Protein as a Natural Inhibitor of Bacterial Endotoxin," 148:532–537 (Jan. 15, 1992).

Weiss, et al., *J. Clin. Invest.*, "Partial Characterization and Purification of a Rabbit Granulocyte Factor That Increases Permeability of *Escheria coli*," 55:33–42 (1975).

Yayon, et al., *Cell*, "Cell Surface, Heparin–like Molecules Are Required for Binding of Basic Fibroplast Growth to its High Affinity Recptor," 64:641–648 (Feb. 22, 1991).

Yong, et al., *Microbial Pathogenesis*, "An experimental mouse model of Yersinia–induced reactive arthritis," 4:305–310 (1988).

Merrifield, et al., *Anal. Chem.*, "Instrument for Automated Synthesis of Peptides," 38(13): 1905–1914 (Dec., 1966).

Merrifield, et al., *J. Am. Chem. Soc.*, "Solid Phase Peptide Synthesis," 85: 2149–2154 (Jul. 20, 1963).

Miles, et al., *VII International Conference on Aids*, Florence, Italy, "Recombinant Platelet Factor 4 (rPF4) and a Non–heparin Binding Derivative Inhibit Aids–Kaposi Sarcoma Derived Cell Lines," Paper 41(8), W.A. 1066 p. 108 (Jun. 16–21, 1991).

Ooi, et al., *J. Exp. Med.*, "Endotoxin–neutralizing Properties of the 25kD N–Terminal Fragment and a New Isolated 30 kD C–Terminal Fragment of the 55–60 kD Bactericidal/Permability–increasing Protein of Human Neutrophils," 174: 649 (1991).

Peacock, et al., *J. Exp. Med.*, "Angiobiogenesis Inhibition Suppresses Collagen Arthritis," 175: 1135–1138 (Apr., 1992).

Repligen Corporation, *Research in Review*, Spring 1992.

Stuart, et al., *J. Clin. Invest.*, "Nature and the Specificity of the Immune Response to Collagen in Type II Collagen–induced Arthritis in Mice," 69: 673–683 (Mar., 1982).

Takayama, et al., *Infect. and Immun.*, "Absence of Lipopoylsaccharide in the Lyme Disease Spirochete," 55(9): 2311–2312 (Sep., 1987).

Taylor, et al., *Nature*, "Protamine is an inhibitor of angiogenesis," 297:307–312 (May 27, 1982).

Tontsch, et al., *Microvascular Res.*, "Isolation, Characterization, and Long–Term Cultivation of Porcine and Murine Cerebral Capillary Endothelial Cells," 37:148–161 (1981).

Weiss, et al., *Blood*, "Cellular and Subcellular Localization of the Bactericidal/Permeability–Increasing Protein of Neutrophils," 69(2): 652–659 (Feb., 1987).

*Primary Examiner*—Charles L. Patterson, Jr.
*Assistant Examiner*—Hydsuk Kim
*Attorney, Agent, or Firm*—Marshall, O'Toole, Gerstein, Murray & Borun

[57] ABSTRACT

The present invention provides therapeutic methods for treatment of conditions including the neutralization of the anti-coagulant activity of heparin, inhibition of angiogenesis, tumor and endothelial cell proliferation, and treatment of chronic inflammatory diseases by administration of bactericidal/permeability-increasing (BPI) protein products.

5 Claims, 31 Drawing Sheets

```
1                            I                              50
                          17-45
VNPGVVVRISQKGLDY ASQQGTAALQKELKRIKIPDYSDSFKIKH LGKGH

60                    II                             100
                          65-99
YSFYSMDIREFQLP SSQISMVPNVGLKFSISNANIKISGKWKAQKRFLK M 110                                            150
SGNFDLSIEGMSISADLKLGSNPTSGKPTITCSSCSSHINS VHVHISKSK

III                                                   199
    142-169
VGWLIQLFHKKIESALRNK MNSQVCEKVTNSVSSELQPYFQTLPVMTKI
```

Fig. 23

THERAPEUTIC USES OF BACTERICIDAL/ PERMEABILITY INCREASING PROTEIN PRODUCTS

This is a continuation of U.S. application Ser. No. 08/093,202, filed Jul. 15, 1993, now abandoned, which is a continuation-in part of U.S. patent application Ser. No. 08/030,644 filed Mar. 12, 1993.

BACKGROUND OF THE INVENTION

The present invention relates to therapeutic uses of bactericidal/permeability increasing (BPI) protein products for the treatment of conditions related to gram-negative bacterial infection and the conditions not directly associated with gram-negative bacterial infection, including neutralization of the anti-coagulant properties of heparin, inhibition of angiogenesis, tumor and endothelial cell proliferation and treatment of chronic inflammatory disease states such as arthritis.

Heparin Binding

Heparin is a heterogeneous group of straight-chain anionic mucopolysaccharides, called glycosaminoglycans having anticoagulant properties. Although others may be present, the main sugars occurring in heparin are: (1) α-L-iduronic acid 2-sulfate, (2) 2-deoxy-2-sulfamino-α-D-glucose 6-sulfate, (3) β-D-glucuronic acid, (4) 2-acetamido-2-deoxy-α-D-glucose, and (5) α-L-iduronic acid. These sugars are present in decreasing amounts, usually in the order (2)>(1)>(4)>(3)>(5), and are joined by glycosidic linkages, forming polymers of varying sizes. Heparin is strongly acidic because of its content of covalently linked sulfate and carboxylic acid groups. Heparin is found within mast cell granules and is released upon degranulation. A cell associated form of heparin is termed heparan sulfate. Heparan sulfate is a broad term used to describe a variety of sulfated proteoglycans (HSPG's) found with a near-ubiquitous distribution on mammalian cell surface membranes and in the extracellular matrix. HSPG contains a variable percentage of sentamaric heparin-like sequences that function in a similar fashion as soluble heparin. The HSPG's serve as a repository for antithrombin III (ATIII) and for heparin-binding growth factors such as fibroblast growth factors (FGF) 1-5, IL-8, GM-CSF and IL-3. Folkman et al., *Inflammation: Basic Principles and Clinical Correlates*, 2d Ed. Chapter 40, pp 821–839 (1992). In fact, cells made genetically deficient in HSPG's require exogenous heparin for growth.

Heparin is commonly administered in doses of up to 400 U/kg during surgical procedures such as cardiopulmonary bypass, cardiac catheterization and hemodialysis procedures in order to prevent blood coagulation during such procedures. The anticoagulant effect of heparin in blood is a result of the interaction of heparin with ATIII. The heparin/ATIII complex is a potent inhibitor of many of the clotting factors of the coagulation cascade. Specific inhibition has been demonstrated for activated Factors IXa, Xa, XIa, XIIIa and thrombin. The heparin/ATIII complex has the highest affinity for Factor Xa and thrombin which are common to both the intrinsic and extrinsic clotting pathways involved as the last two steps of the clotting cascade that results in the conversion of fibrinogen to fibrin.

When heparin is administered for anticoagulant effects during surgery, it is an important aspect of post-surgical therapy that the effects of heparin are promptly neutralized so that normal coagulation function can be restored. Currently protamine is used to neutralize heparin. Protamines are simple proteins of low molecular weight which are commonly isolated from salmon sperm. They are rich in arginine amino acid residues and strongly basic. Administered alone, prommines (usually in the form of prommine sulfate) have anti-coagulant effects. When administered in the presence of heparin, a stable complex is formed and the anticoagulant activity of both drugs is lost. Significant hypotensive and anaphylactoid effects of prommine have limited its clinical utility.

Other reported compounds which have heparin neutralizing activity include platelet factor 4 (PF4) and major basic protein, see U.S. Pat. No. 5,086,164. Major basic protein demonstrates heparin neutralizing activity but is also highly toxic.

Angiogenesis

Angiogenesis is closely associated with endothelial cell proliferation and constitutes the development of new capillary blood vessels. As such, it is an important process in mammalian development and growth, and in menstruation processes. The release of angiogenic growth factors, such as fibroblast growth factors 1–5, induces proliferation of endothelial cells via a heparin-dependent receptor binding mechanism. See Yayon et al., *Cell*, 64:841–848 (1991). These heparin-binding growth factors can be released due to vascular trauma (wound healing), immune stimuli (autoimmune disease), inflammatory mediators (prostaglandins) and from tumor cells.

Angiogenesis is also associated with a number of pathological conditions in which it would be desirable to inhibit such new blood vessel development. As one example, angiogenesis is critical to the growth, proliferation, and metastasis of various tumors. Other pathological conditions associated with angiogenesis include diabetic retinopathy, retrolental fibroplasia, neovascular glaucoma, psoriasis, angiofibromas, immune and non-immune inflammation including rheumatoid arthritis, capillary proliferation within atherosclerotic plaques, hemangiomas, endometriosis and Kaposi's Sarcoma.

Folkman et al., supra, discloses that psoriatic lesions in the skin are dominated by epithelial proliferation, neovascularization, and an infiltrate of inflammatory cells. It is unclear, however, whether angiogenesis is a step in the pathogenesis of psoriasis or a secondary phenomenon.

Several substances are known to function as angiogenesis inhibitors and have been reported to inhibit tumor angiogenesis, to prevent the onset of arthritis and to inhibit established arthritis in collagen-induced arthritis models, Peacock et al., *J. Exp. Med.*, 175, 1135–1138 (1992). As one example, protamine is known to inhibit tumor angiogenesis and subsequent tumor growth. According to Taylor et al., *Nature*, 297:307–312 (1982) protamine's anti-angiogenic activity is attributed to is ability to bind heparin. PF4 is also known to exhibit anti-angiogenic activity. Of interest to the present application is U.S. Pat. No. 5,112,946 which discloses modified PF4 and analogs thereof which have anti-angiogenic activity but lack the ability to bind heparin. PF4 has been shown to have at least two functional properties. Heparin binding has been studied most extensively; however, PF4 was originally described to have collagenase inhibitory properties. Collagenase inhibitors were the first inhibitors of angiogenesis to be discovered. See Folkman, 1973, supra. The mutations in the heparin binding region of PF4 were not examined for their effect on collagenase inhibitory activity. Interestingly, thrombospondin is also an inhibitor of angiogenesis and binds to heparin with a serine/tryptophan motif instead of a basic amino acid motif. Thus, there is no obvious single consensus sequence heparin binding or for angiogenesis inhibition.

Published PCT patent application WO 92/01003 discloses the use of glycosaminoglycan (heparin) derivatives and their use as inhibitors of tumor invasiveness. Heparin derivatives are disclosed which are described as being substantially devoid of anticoagulation activity and which impede the formation of tumor metastases in a host.

Chronic Inflammation

Chronic inflammation is usually accompanied by angiogenesis. Arthritis is a chronic syndrome characterized by the inflammation of the peripheral joints accompanied by synovial thickening and the influx of immune factors and cells such as polymorphonuclear leukocytes (PMN). In rheumatoid arthritis, the inflammation is immune driven, while in reactive arthritis, inflammation is associated with infection of the synovial tissue with pyogenic bacteria or other infectious agents. Folkman et al., 1973, supra, also note that many types of arthritis progress from a stage dominated by an inflammatory infiltrate in the joint to a later stage in which a neovascular pannus invades the joint and begins to destroy cartilage. While it is unclear whether angiogenesis in arthritis is a causative component of the disease, and not an epiphenomenon, there is evidence that angiogenesis is necessary for the maintenance of synovitis in rheumatoid arthritis. While nonsteroidal anti-inflammatory drugs (NSAIDs), corticosteroids and other therapies have provided improvements in relief for treatment of arthritis, there remains a need in the art for more effective therapies for arthritis and other inflammatory diseases.

Inflammation and angiogenesis are now understood to be separable but not mutually exclusive processes. Specific angiogenic proteins have been discovered that stimulate angiogenesis without inflammation whereas angiostatic steroids can inhibit angiogenesis without decreasing acute inflammation. See Folkman, 1973, supra. Interestingly, endotoxin has been identified as the most potent exogenous stimulator of angiogenesis through its stimulation of macrophage cytokines and growth factors.

Bactericidal/Permeability-Increasing Protein

Bactericidal/permeability-increasing protein (BPI) is a protein isolated from the granules of mammalian PMNs, which are blood cells essential in the defense against invading microorganisms. Human BPI protein has been isolated from polymorphonuclear neutrophils by acid extraction combined with either ion exchange chromatography [Elsbach, *J. Biol. Chem.*, 254:11000 (1979)] or *E. coli* affinity chromatography [Weiss, et al., Blood, 69:652 (1987)], referred to herein as natural BPI, and has potent bactericidal activity against a broad spectrum of gram-negative bacteria. The molecular weight of human BPI is approximately 55,000 daltons (55 kD). The amino acid sequence of the entire human BPI protein, as well as the DNA encoding the protein, have been elucidated in FIG. 1 of Gray et al., *J. Biol. Chem.*, 264:9505 (1989), incorporated herein by reference.

The bactericidal effect of BPI has been shown to be highly specific to sensitive gram-negative species, while non-toxic for other microorganisms and for eukaryotic cells. The precise mechanism by which BPI kills bacteria is as yet unknown, but it is known that BPI must first attach to the surface of susceptible gram-negative bacteria. This initial binding of BPI to the bacteria involves electrostatic interactions between the basic BPI protein and the negatively charged sites on lipopolysaccharides (LPS). LPS has been referred to as "endotoxin" because of the potent inflammatory response that it stimulates. LPS induces the release of mediators by host inflammatory cells which may ultimately result in irreversible endotoxic shock. BPI binds to lipid A, the most toxic and most biologically active component of LPS.

In susceptible bacteria, BPI binding is thought to disrupt LPS structure, leading to activation of bacterial enzymes that degrade phospholipids and peptidoglycans, altering the permeability of the cell's outer membrane, and initiating events that ultimately lead to cell death. Elsbach and Weiss, *Inflammation: Basic Principles and Clinical Correlates*, eds. Gallin et al., Chapter 30, Review Press, Ltd. (1992). BPI is thought to act in two stages. The first is a sublethal stage that is characterized by immediate growth arrest, permeabilization of the outer membrane and selective activation of bacterial enzymes that hydrolyze phospholipids and peptidoglycan. Bacteria at this stage can be rescued by plating on serum albumin supplemented media. The second stage, defined by growth inhibition that cannot be reversed by serum albumin, occurs after prolonged exposure of the bacteria to BPI and is characterized by extensive physiologic and structural changes, including penetration of the cytoplasmic membrane.

BPI is also capable of neutralizing the endotoxic properties of LPS to which it binds. Because of its gram-negative bactericidal properties and its ability to neutralize LPS, BPI can be utilized for the treatment of mammals suffering from diseases caused by gram-negative bacteria, such as bacteremia or sepsis.

A proteolytic fragment corresponding to the N-terminal portion of human BPI holoprotein possesses the lipid A binding and antibacterial activity of the naturally-derived 55 kD human holoprotein. In contrast to the N-terminal portion, the C-terminal region of the isolated human BPI protein displays only slightly detectable anti-bacterial activity. Ooi, et al., *J. Exp. Med.*, 174:649 (1991). A BPI N-terminal fragment, comprising approximately the first 199 amino acid residues of the human BPI holoprotein and referred to as "rBPI$_{23}$", has been produced by recombinant means as a 23 kD protein. Gazzano-Santoro et al., *Infect. Immun.* 60:4754–4761 (1992).

Of interest to the present application are the disclosures in PCT International application PCT/US91/05758 having publication No. WO 92/03535 relating to compositions comprising a BPI protein and an anionic compound which compositions are said to exhibit (1) no bactericidal activity and (2) endotoxin neutralizing activity. Anionic compounds are preferably a protein such as serum albumin but can also be a proteoglycan such as heparin. In addition, Weiss et al., *J. Clin. Invest.*, 55:33–42 (1975) discloses that heparin sulfate and LPS bind to block expression of the permeability increasing activity of BPI. Neither reference discloses neutralization of heparin by combination with BPI, however.

There continues to exist a need in the art for new products and methods for use in neutralization of heparin, inhibition of tumor and angiogenesis, endothelial cell proliferation and treatment of chronic inflammation.

SUMMARY OF THE INVENTION

According to one aspect of the invention, methods are provided for neutralizing the anti-coagulant activity of heparin comprising administering an effective amount of a BPI protein product in vivo to a subject or in vitro to a fluid sample containing heparin.

According to another aspect of the invention, a BPI protein product is administered to subjects in order to inhibit endothelial cell proliferation including but not limited to endothelial cell proliferation associated with angiogenesis. The invention provides methods of inhibiting angiogenesis associated with a variety of clinical conditions. Specifically provided by the invention are methods of treating cancer by inhibiting angiogenesis associated with malignant tumor proliferation; Kaposi's sarcoma lesions and the like. Cancers susceptible to treatment by administration of BPI protein products include melanoma, sarcomas, and carcinomas including but not limited to breast, colon, lung, and prostate carcinomas. Other conditions for which BPI protein products can be administered for inhibition of angiogenesis include ocular retinopathy, retrolental fibroplasia, psoriasis, angiofibromas, endometriosis, hemangiomas and the like. Also contemplated by the invention are methods of contraception comprising delivering of an effective amount of a BPI protein product so as to prevent implantation of a fertilized ovum.

The invention also provides methods of treating chronic inflammatory disease states such as arthritis, psoriasis, inflammatory bowel disease, Crohn's disease, ulcerative colitis, lupus erythematosus, autoimmune uveitis, Lyme disease, and asthma comprising administering an effective amount of a BPI protein product to a subject suffering from the inflammatory disease state.

The invention also provides methods of preparation of medicaments for neutralization of the anti-coagulant properties of heparin, inhibition of tumor and endothelial cell proliferation, inhibition of angiogenesis and treatment of chronic inflammatory disease states.

Such medicaments can be prepared for oral administration for injection or other parenteral methods and preferably include conventional pharmaceutically acceptable carriers and adjuvants as would be known to those of skill in the art. The medicaments are preferably in the form of a unit dose in solid, semi-solid and liquid dosage forms such as tablets, pills, powders, liquid solutions or suspensions, and injectable and infusible solutions. Effective dosage ranges from about 100 µg/kg to about 10 mg/kg of body weight are contemplated. As used herein, "BPI protein product" includes naturally and recombinantly produced bactericidal/permeability-increasing protein; natural, synthetic, and recombinant biologically active polypeptide fragments of bactericidal/permeability increasing protein; and biologically active polypeptides or analogs, including hybrid fusion proteins, of either bactericidal/permeability increasing protein or biologically active fragments thereof.

BRIEF DESCRIPTION OF THE FIGURES

FIG. 23 depicts the functional domains of $rBPI_{23}$.

DETAILED DESCRIPTION

Figure 1:
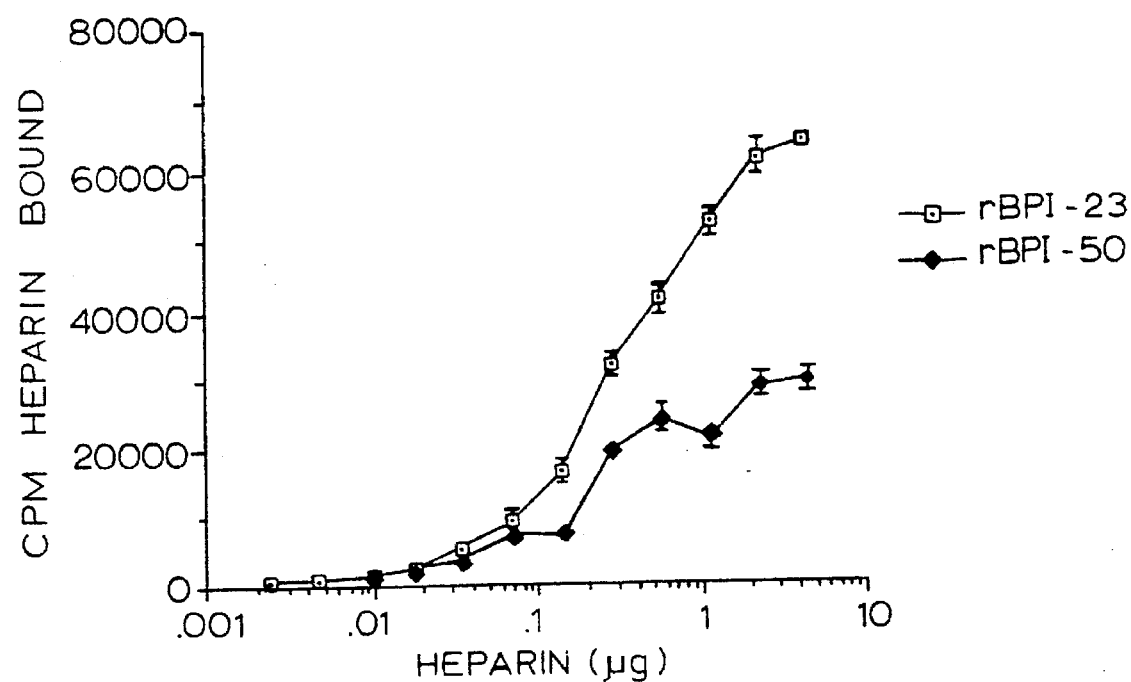
FIG. 1 depicts a graph of a heparin binding assay for $rBPI_{23}$ and rBPI.

The present invention relates to the administration of bactericidal/permeability-increasing protein (BPI) protein products for the treatment of a variety of therapeutic conditions not directly associated with bacterial infection.

While BPI protein products as described herein are useful as potent cytotoxins for gram-negative bacteria and for neutralizing the adverse effects of lipopolysaccharides associated with the cell walls of gram-negative bacteria, a variety of therapeutic effects for BPI protein products not directly associated with the gram-negative bacterial infection have been discovered. Specifically, the invention provides methods for treating conditions not directly associated with gram-negative infections including neutralization of the anti-coagulant activity of heparin, inhibition of tumor and endothelial cell proliferation including cell proliferation associated with angiogenesis and treatment of chronic inflammatory disease states such as arthritis.

The BPI protein products including biologically active fragments of BPI holoprotein which are to be administered according to the methods of this invention may be generated and/or isolated by any means known in the art. Co-owned, copending U.S. patent application Ser. No. 07/885,501, and a continuation-in-part thereof, U.S. patent application Ser. No. 08/072,063 filed May 19, 1993 which are both hereby incorporated by reference, disclose novel methods for the purification of recombinant BPI protein products expressed in and secreted from genetically transformed mammalian host cells in culture and discloses how one may produce large quantities of recombinant BPI products suitable for incorporation into stable, homogeneous pharmaceutical preparations.

Biologically active fragments of BPI include biologically active molecules that contains the same amino acid sequence as a BPI holoprotein, except that the molecule lacks amino-terminal amino acids, internal amino acids, and/or carboxy-terminal amino acids of the holoprotein. By way of nonlimiting examples, such fragments include those described herein and the previously mentioned natural 25 kD fragment and a recombinant 23 kD, 199 amino acid residue amino-terminal fragment of the human BPI holoprotein referred to as rBPI$_{23}$. See, Gazzano-Santoro et al., Infect. Immun. 60:4754–4761 (1992). In that publication, an expression vector was used as a source of DNA encoding a recombinant expression product (rBPI$_{23}$) having the 31-residue signal sequence and the first 199 amino acids of the N-terminus of the mature human BPI, as set out in SEQ ID NOs: 1 and 2 taken from Gray et al., supra, except that valine at position 151 is specified by GTG rather than GTC and residue 185 is glutamic acid (specified by GAG) rather than lysine (specified by AAG). Recombinant holoprotein referred to herein as rBPI or rBPI$_{50}$ has also been produced having the sequence set out in SEQ ID NOs: 1 and 2 taken from Gray et al., supra, with the exceptions noted for rBPI$_{23}$.

Other non-limiting examples of biologically active fragments of BPI include fragments of, e.g., the BPI holoprotein or of rBPI$_{23}$ generated upon subjecting the proteins to chemical cleavage with agents such as cyanogen bromide (CNBr) or enzymatic digestion with agents such as endoproteinase Asp-N. BPI protein fragments may also be provided in the form of linear or cyclic synthetic peptides comprising replicas of from about 5 to about 50 continuous amino acids within the BPI holoprotein and especially within the amino terminal half of the protein. Such peptides may be provided in monomeric form, in the form of dimers or multimers (where the peptide replicates a region of BPI having cysteine residues) and in the form of "linear" dimers or multimers wherein a BPI sequence is present repeatedly in the peptide, with or without separation by "spacer" amino acids allowing for selected conformational presentation.

Biologically active analogs of BPI include but are not limited to recombinant hybrid fusion proteins comprising BPI holoprotein or biologically active fragment thereof, and at least a portion of at least one other polypeptide. Such proteins are described by Theofan et al. in co-owned, copending U.S. patent application Ser. No. 07/885,911, and a continuation-in-part application thereof, U.S. patent application Ser. No. 08/064,693 filed May 19, 1993 which are incorporated herein by reference in their entirety and include hybrid fusion proteins comprising, at the amino terminal end, a BPI protein or a biologically active fragment thereof and, at the carboxy terminal end, at least one constant domain of an immunoglobulin heavy chain or allelic variant thereof.

Biologically active analogs of BPI also include but are not limited to BPI protein products wherein one or more amino acid residues has been replaced by a different amino acid or by atypical amino acids. For example, co-owned, copending U.S. patent application Ser. No. 08/013,801 (Theofan et al., "Stable Bactericidal/Permeability-Increasing Protein Products and Pharmaceutical Compositions Containing the Same"), filed Feb. 2, 1993, which is incorporated herein by reference, discloses polypeptide analogs of BPI and BPI fragments wherein a cysteine residue at position 132 or at position 135 is replaced by a different amino acid. One preferred protein product designated rBPI$_{23}\Delta$ cys comprises the first 199 amino acid residues of BPI holoprotein but wherein the cysteine residue at position 132 is substituted with an alanine. "U.S. Ser. No. 08/013,801, now U.S. Pat. No. 5,420,019, also discloses N-terminal fragments of BPI protein having molecular weights of approximately 21 kD."

The administration of BPI protein products is preferably accomplished with a pharmaceutical composition comprising a BPI protein product and a pharmaceutically acceptable diluent, adjuvant, or carrier. The BPI protein product composition may be administered without or in conjunction with known antibiotics, surfactants, or other chemotherapeutic agents. A preferred pharmaceutical composition containing BPI protein products comprises BPI at a concentration of 1 mg/ml in citrate buffered saline (0.02M citrate, 0.15M NaCl, pH 5.0) comprising 0.1% by weight of poloxamer 188 (Pluronic F-68, BASF Wyandotte, Parsippany, N.J.) and 0.002% by weight of polysorbate 80 (Tween 80, ICI Americas Inc., Wilmington, Del.). Such preferred combinations are described in co-owned, copending, U.S. patent application Ser. No.08/012,360 (McGregor et al., "Improved Pharmaceutical Composition"), filed Feb. 2, 1993, the disclosure of which is incorporated herein by reference.

Effective doses of BPI and BPI protein products for partial or complete neutralization of the anti-coagulant activity of heparin and other effects described herein may be readily determined by those of skill in the art according to conventional parameters including the size of the subject, the quantity of heparin administered to the subject and the time since administration of the heparin.

Other aspects and advantages of the present invention will be understood upon consideration of the following illustrate examples. Example 1 addresses assay systems for quantification of heparin binding by BPI protein products; Example 2 describes the relative capacity of heparin to block binding of bacterial LPS to BPI protein products; Examples 3 and 4, respectively, present results of tests for the capacity of BPI protein products to inhibit thrombin or Factor Xa inactivation by antithrombin III/heparin complexes; and Example 5 relates to the effect of BPI protein products on heparin-mediated lengthening of thrombin time. Example 6 relates to the effect of BPI protein products on heparin mediated lengthening of partial thromboplastin time. Examples 7–9 relate to administration of BPI protein products in model systems of in collagen and bacterial induced arthritis animal model systems exemplifying treatment of chronic inflammatory disease states. Examples 10–11 illustrate testing of BPI protein products for angiostatic effects in a mouse malignant melanoma metastasis model system. Example 12 addresses effects of BPI protein products on endothelial cell proliferation and possible binding mechanisms involved. Example 13 relates to preparation of synthetic BPI peptides. Examples 14–16 illustrate heparin-binding, LPS-binding and bactericidal activities for the synthetic BPI peptides of Example 13. Example 17 relates to preparation of additional synthetic BPI peptides. Examples 18 through 21 address properties of the peptides of Example 17. Example 22 discloses the preparation of BPI proteolytic fragment peptides. Example 23 discloses the bactericidal effects of the BPI proteolytic fragments. Example 24 discloses the heparin binding properties of the BPI proteolytic fragments. Example 25 discloses the effect of BPI proteolytic fragments on an LAL assay.

EXAMPLE 1

HEPARIN BINDING BY BPI PROTEIN PRODUCTS

Heparin binding assays were conducted using membrane bound natural and recombinant BPI molecules and radiolabelled heparin. Briefly, rBPI$_{23}$ and holoprotein designated rBPI or rBPI$_{50}$ were added to wells of a 96-well microtiter plate having an Immobilon-P (Millipore, Bedford, Mass.) membrane disposed at the bottom of the wells. Five µg of protein was added to each well. The wells were dried and subsequently blocked with a 0.1% bovine serum albumin (BSA) in phosphate buffered saline, pH 7.4 (blocking buffer.) Dilutions of $^3$H-heparin (DuPont, NEN, Wilmington, Del.) were made in the blocking buffer and incubated in the BPI containing wells for one hour at 4° C. The unbound heparin is aspirated and the wells were washed three times with blocking buffer, dried and removed for quantitation in a liquid scintillation counter. Typical assay results are graphically presented in FIG. 1. While BSA in the blocking buffer does have a low affinity and capacity to bind heparin, this was considered physiologically irrelevant and the background was routinely subtracted from the test compound signal. The binding of radiolabeled heparin was completely inhibited by a 100 fold excess of unlabeled heparin (dam not shown).

Similar assays compared heparin binding by rBPI$_{23}$, rBPI$_{50}$, and natural holoprotein (BPI) with thaumatin control protein (having charge and size similar to rBPI$_{23}$) or with a wash buffer (1% BSA) control. In these assays, less heparin binding by the natural and recombinant BPI holoproteins was observed. The lesser extent of binding by rBPI and nBPI may have been the result of carbohydrate contamination of the protein preparations.

In addition, binding constants with $^3$H-heparin as the ligand were determined using nonlinear function minimization with Grafit software (Erithicus Software Ltd., Staines, UK) for rBPI$_{23}$, rBPI, protamine sulfate (Sigma Chemical Co.) and thaumatin with the results shown in Table 1 below.

TABLE 1

Binding Constants with $^3$H-heparin as the Ligand

| PROTEIN | $K_d$ | CAPACITY | HEPARIN COLUMN NaCl ELUTION |
|---|---|---|---|
| rBPI$_{23}$ | 79 nM | 2.63 µg | 0.84 M |
| rBPI$_{50}$ | 173 nM | 1.30 µg | 0.81 M |
| Protamine | 8.1 nM | 2.66 µg | 1.33 M |
| Thaumatin | no binding | | 0.15 M |

EXAMPLE 2

HEPARIN COMPETITION FOR BPI PROTEIN PRODUCT BINDING

Figure 2:
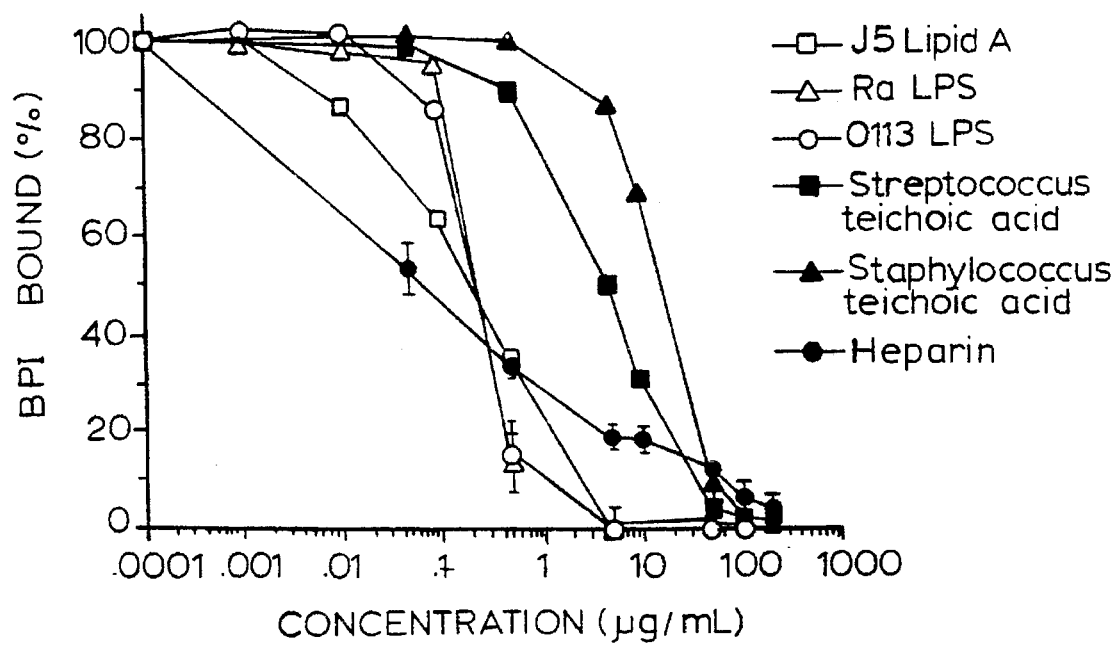
FIG. 2 depicts a graph showing the effect of heparin on $rBPI_{23}$ binding to $E.\ coli$ J5 lipid A compared to various LPS and teichoic acid samples.

The ability of heparin, soluble lipid A, LPS, and Teichoic acids to compete with immobilized E. coli J5 lipid A for binding to soluble rBPI$_{23}$ was assessed. Specifically, Immulon 2 (Dynatech, Chantilly, Va.) microtiter wells were coated with E. coli J5 lipid A at a concentration of 0.5 µg/mL in methanol (50 µL volume). The wells were then blocked for 4 hours at 37° C. with PBS containing 0.1% BSA. Control wells were treated with 50 µL of plain methanol and then blocked as above. The blocked wells were aspirated and washed twice with PBS/0.05% Tween-20. Varying concentrations of putative inhibitors were plated onto the wells in a volume of 25 µL PBS, followed by 200,000 cpm of radio-iodinated rBPI$_{23}$ in 25 µL of PBS containing 0.1% Tween-20. The test solutions included Ra LPS from Salmonella minnesota R60 at 200 µL; smooth LPS from E. coli 0113 (RIBI Immunochem, Hamilton, Mont., #R318) at 200 µg/mL; lipoteichoic acid from Streptococcus faecalis, (Sigma, St. Louis, Mo., #L-4015) at 400 µg/mL; lipoteichoic acid from Staphylococcus Aureus, (Sigma #L-2525) at 400 µg/mL; and heparin sodium USP injection (Lypho-Med, Rosemont, IL, #9155-01) at 400 µg/mL. Binding was allowed to proceed overnight at 4° C. with gentle shaking, after which the wells were aspirated, washed three times with PBS/0.05% Tween-20, and counted. The results as set out in FIG. 2 show a high affinity of rBPI$_{23}$ for heparin and also that heparin blocks BPI binding to lipid A.

EXAMPLE 3

HEPARIN NEUTRALIZATION BY BPI PROTEIN PRODUCTS: EFFECT OF BPI ON THROMBIN INACTIVATION BY ATIII/HEPARIN COMPLEXES

A chromogenic assay was used to determine the effect of rBPI$_{23}$ on thrombin inactivation by ATIII/heparin complexes. Specifically, a Chromostrate™ anti-thrombin assay kit (Organon Teknika Corp., Durham, N.C.) was used to examine the inhibition of purified thrombin by preformed ATIII/heparin complexes in plasma.

Figure 3:
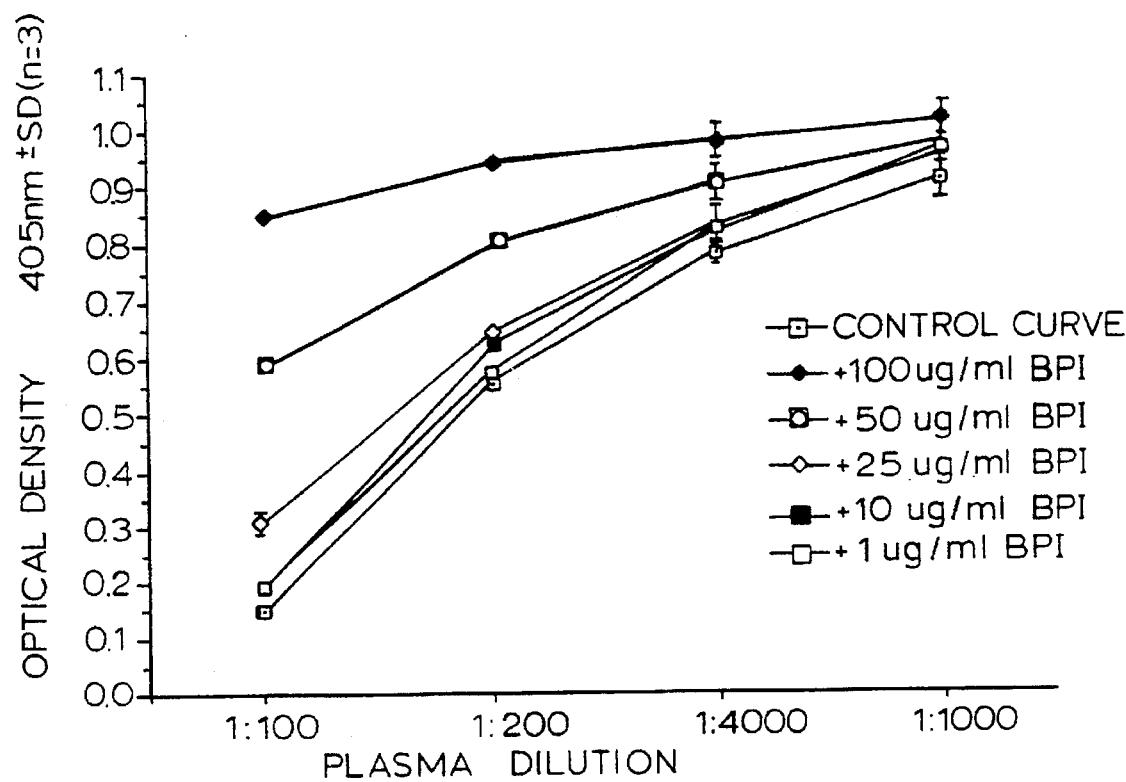
FIG. 3 depicts a graph showing the effect of $rBPI_{23}$ on ATIII/heparin inhibition of thrombin.

The assay was performed in 96 well microtiter plates in triplicate with a final volume per well of 200 µL. The order of addition of assay components was as follows: 1) 50 µl sample (rBPI$_{23}$ or thaumatin as a control protein) with final concentrations of 100, 50, 25, 10 and 1 µg/well in PBS; 2) 50 µl plasma 1:100 in buffer; 3) 50 µl thrombin at 1 nKat/mL in buffer; and 4) 50 µl chromogenic substrate 1 µmol/mL in H$_2$O. The reaction was allowed to proceed for 10 minutes at 37° C. and stopped with 50 µL 0.1M citric acid and the color reaction was quantitated on a microplate reader. The assay results shown in FIG. 3 indicate that rBPI$_{23}$ can effectively neutralize ATIII/heparin complexes in heparinized human plasma in a dose dependent manner. As the plasma was titrated the amount of thrombin activity increased. This was caused by a decrease in the amount of inhibitory ATIII/heparin complexes in the added plasma. The control protein, thaumatin, showed no similar neutralizing effect and was essentially equivalent to the buffer control at all protein concentrations.

EXAMPLE 4

HEPARIN NEUTRALIZATION BY BPI PROTEIN PRODUCTS: EFFECT OF BPI ON FACTOR Xa INACTIVATION BY ATIII/HEPARIN COMPLEXES

A chromogenic assay was used to determine the effect of rBPI$_{23}$ on Factor Xa neutralization by ATIII/heparin complexes. Specifically, the assay was conducted using a chromostrate heparin anti-Factor Xa assay kit (Organon Teknika Corp.) and was performed under fixed concentrations of Factor Xa and ATIII. Heparin concentration was varied so that a heparin standard curve was generated for heparin at concentrations of 1, 0.5, 0.25, 0.125, 0.063, 0.031, 0.016, 0.008, 0.004, 0.002, and 0 units/mL in PBS. The assay measured functional Factor Xa activity by the release of a chromogenic compound from a synthetic substrate. ATIII/heparin complexes neutralize Factor Xa activity, thus the amount of chromogen released was inversely related to the amount and anti-Factor Xa activity of heparin in the assay sample.

Figure 4:
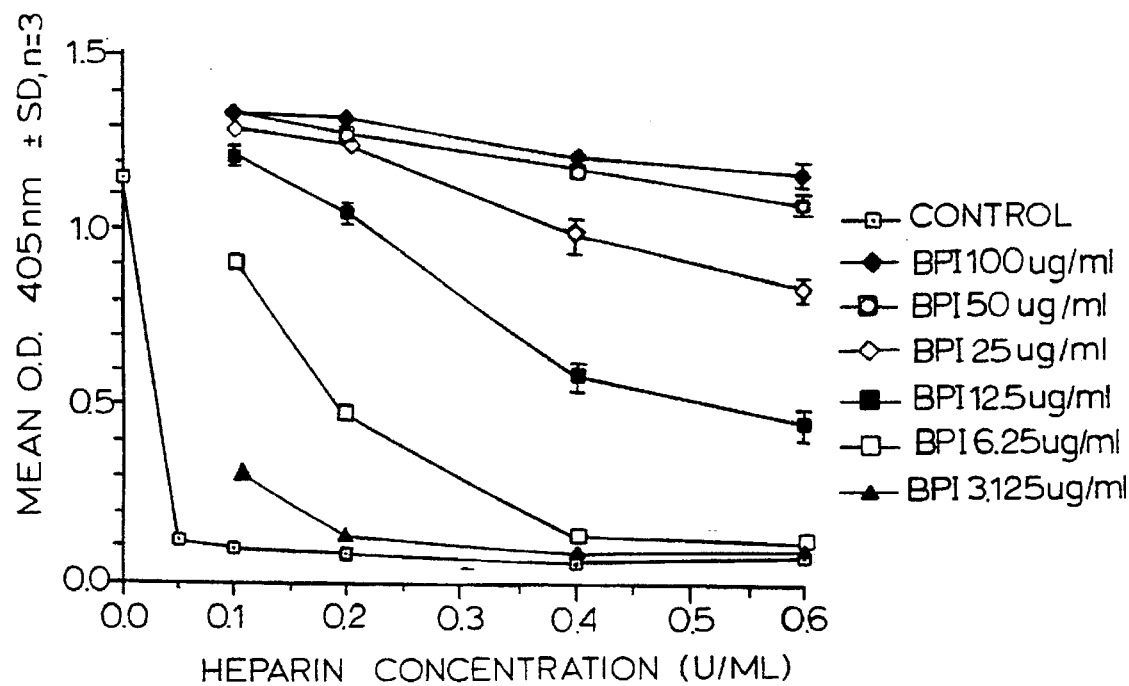
FIG. 4 depicts a graph showing the effect of $rBPI_{23}$ on ATIII/heparin inhibition of Factor Xa.

The assay was performed in 96 well microtiter plates in triplicate with a final volume per well of 200 µL. Assay components were added to the microtiter wells as follows: 1) 50 μL samples (rBPI$_{23}$ or thaumatin as a control protein) with final concentrations of 100, 50, 25, 10 and 1 μg/well in PBS; 2) 50 μL Factor Xa 0.14/nKat/mL in H$_2$O; 3)25 μL ATIII at 0.5 U/mL in H$_2$O; 4) 24 μL heparin at 0.25 U/mL in buffer; 5) 50 μL substrate (3 μmoles/mL). The reaction was allowed to proceed for 10 minutes at 37° C. and stopped with 50 μl of 0.1M citric acid and then the color reaction was quantitated on a microplate reader. The assay results shown in FIG. 4 indicates that rBPI$_{23}$ can effectively neutralize heparin in the ATIII/heparin inhibition of Factor Xa. As the concentration of heparin is increased, the amount of rBPI$_{23}$ necessary for heparin neutralization also increased. The control protein, thaumatin, showed no similar neutralizing effects and was essentially equivalent to the buffer control at all protein concentrations.

EXAMPLE 5

HEPARIN NEUTRALIZATION BY BPI PROTEIN PRODUCTS: EFFECT OF BPI ON HEPARIN-MEDIATED LENGTHENING OF THROMBIN TIME

Figure 5:
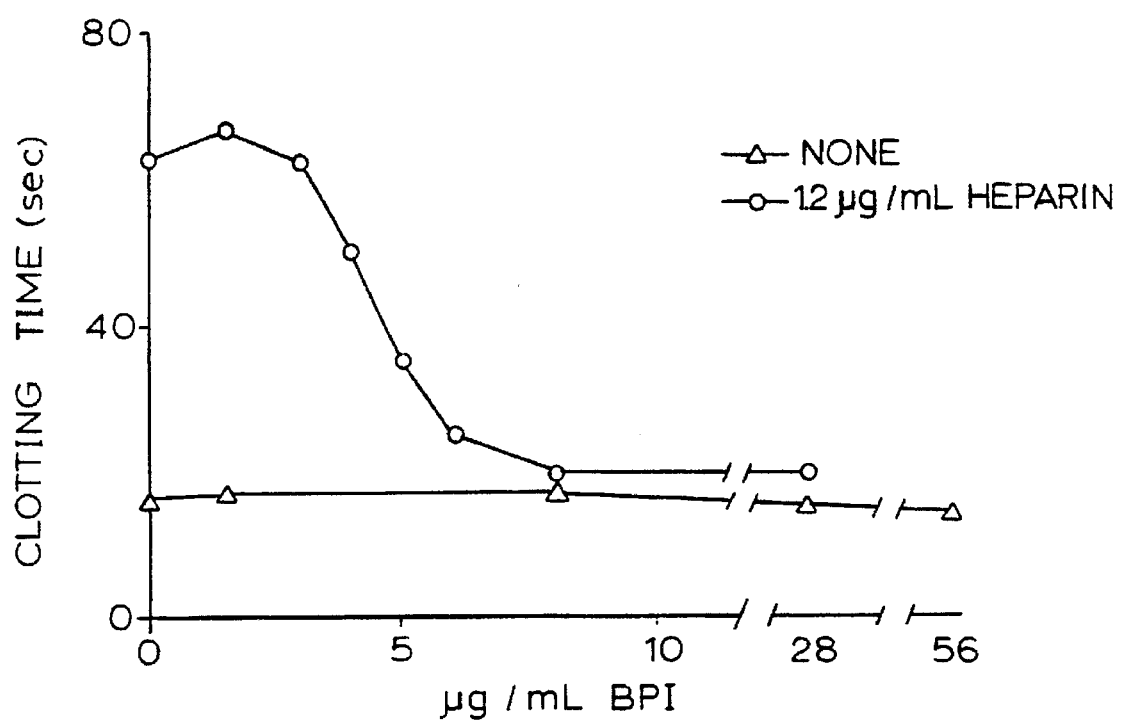
FIG. 5 depicts a graph showing the effect of $rBPI_{23}$ on heparin-mediated lengthening of thrombin time in human plasma.

The effect of BPI protein products on heparin-mediated lengthening of thrombin time, i.e., the time required for clotting of a mixture of thrombin and plasma was examined. Thrombin time is lengthened by the presence of endogenous or exogenous inhibitors of thrombin formation, such as therapeutically administered heparin. Agents which neutralize the anti-coagulant effects of heparin will reduce the thrombin time measured by the test. Human citrated plasma (200 μL) was incubated for 1 minute at 37° C. with either 15 μL of diluent (0.15M NaCl, 0.1M Tris, pH 7.4) or 15 μL of the diluent also containing 25 μg/mL heparin (187 units/mg). Various concentrations of rBPI$_{23}$ (from 0.0 to 56 μg/mL) in a volume of 15 μL were added, followed immediately by 100 μL of thrombin reagent (Sigma Chemical Co., No. 845–4). Clotting time (thrombin time) was measured using a BBL Fibrometer (Becton Dickinson Microbiology Systems, Cockeysville, Md.). The results shown in FIG. 5 establish that rBPI$_{23}$ inhibits the heparin-mediated lengthening of thrombin time. In the absence of heparin, rBPI$_{23}$ had no effect on the assay even at concentrations as high as 56 μg/mL.

EXAMPLE 6

HEPARIN NEUTRALIZATION BY BPI PROTEIN PRODUCTS: EFFECT OF BPI ON PARTIAL THROMBOPLASTIN TIME

Figure 6:
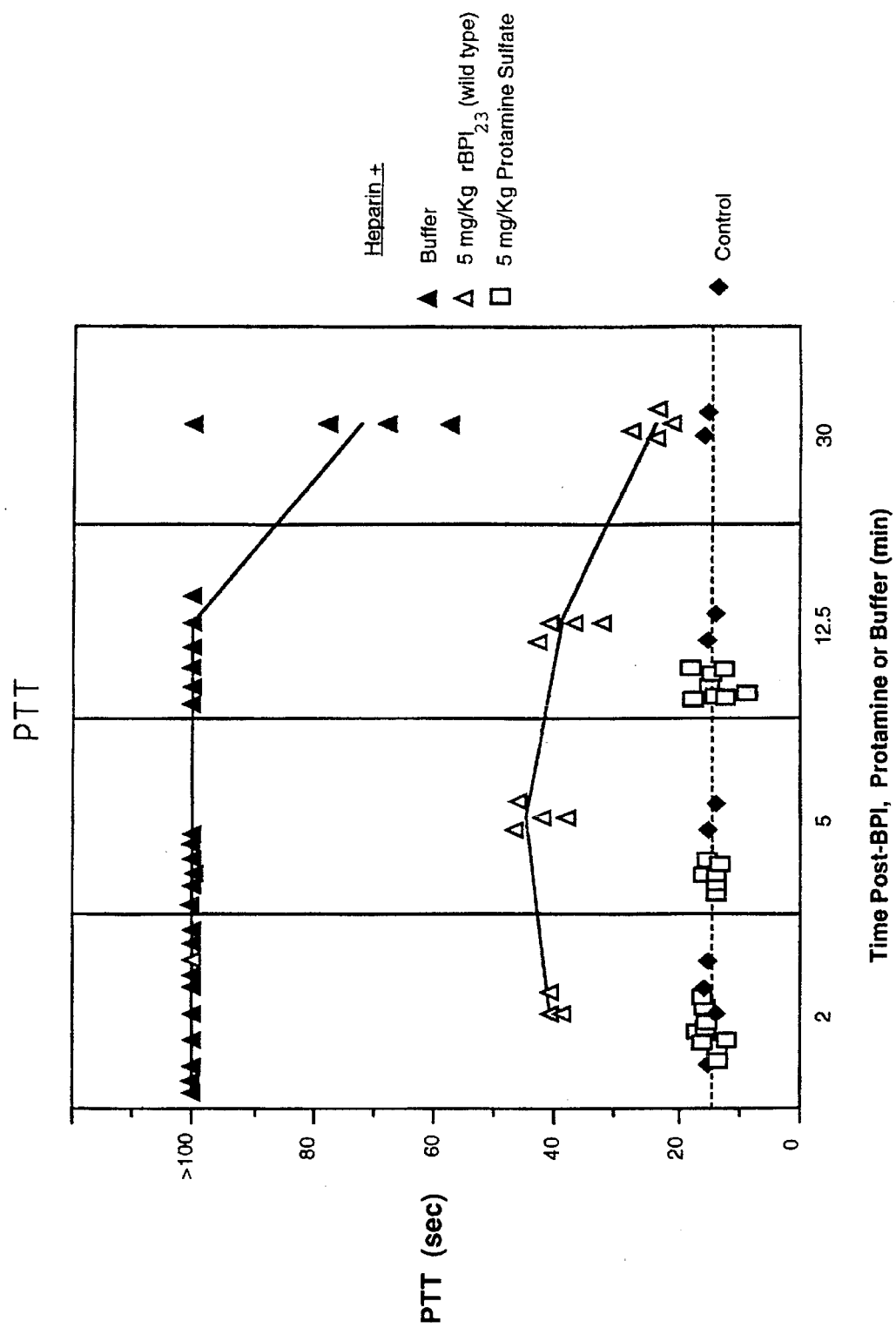
FIG. 6 depicts a graph showing the effect of $rBPI_{23}$ on partial thromboplastin time.

The effect of rBPI$_{23}$, or protamine sulfate on partial thromboplastin time (FFT) in heparinized rats was determined. PTT is lengthened by the presence of endogenous or exogenous inhibitors of thrombin formation, such as therapeutically administered heparin. Agents which neutralize the anti-coagulant effects of heparin will reduce the PTT as measured by the test. Sprague-Dawley rats housed under NIH guidelines were administered with 100 U/kg heparin by bolus intravenous injections via the animals' tail vein followed by administration of 5 mg/kg rBPI$_{23}$, 5 mg/kg protamine sulfate or buffer. The PTT was then determined from blood samples collected from the abdominal aorta of the previously anesthetized animals. The PTT of untreated animals was also determined. The results shown in FIG. 6 establish that both rBPI$_{23}$ and protamine had an immediate effect on the PTT of the treated animals. These animal data confirm the heparin neutralizing effects of BPI protein products as shown in Examples 2–5.

The collective results from Examples 1 through 6 show that rBPI$_{23}$ binds to heparin in direct binding assays and effectively neutralizes heparin inhibition of coagulation proteases. Based on these characteristics, BPI protein products are projected to be useful in the clinical neutralization of heparin anti-coagulant effects in dosages generally corresponding functionally to those recommended for protamine sulfate, but are not expected to possess the severe hypotensive and anaphylactoid effects of that material.

EXAMPLE 7

THERAPEUTIC EFFECTS OF BPI PROTEIN PRODUCTS FOR CHRONIC INFLAMMATORY DISEASE: COLLAGEN INDUCED ARTHRITIS MODEL

A further aspect of the present invention relates to the discovery of the utility of BPI to treat and prevent the effects of chronic inflammatory disease states such as arthritis, including rheumatoid and reactive arthritis, psoriasis, inflammatory bowel disease, Crohn's disease, ulcerative colitis, lupus erythematosus, autoimmune uveitis, Lyme disease, and asthma. Exemplary methods are provided for treating subjects suffering from arthritis comprising administering an effective amount of a BPI protein product in order to prevent or treat arthritis. The BPI protein product may be administered topically, or by injection such as intraarticularly, intravenously, intramuscularly or subcutaneously or by other parenteral and non-parenteral methods.

The effect of administration of BPI protein products was studied in a collagen-induced arthritis model. Specifically, arthritis was induced in mice by intradermal immunization of bovine Type II collagen at the base of the tail according to the method of Smart et al., *J. Clin. Invest.*, 69:673–683 (1982). Generally, mice begin to develop arthritic symptoms at Day 21 after collagen immunization. The arthritic scores of the treated mice were then evaluated in a blinded fashion over a period of 120 days for mice treated on each of days 21–25 with doses of either rBPI$_{23}$, thaumatin control protein, or buffer which were injected intravenously via the tail vein.

Specifically, bovine Type II collagen (Southern Biotechnology Associates, Inc., Birmingham Ala.) was administered via intradermal injection (0.1 mg/mouse) at the base of the tail on day 0 to groups of ten male mice (Mouse/DBA/1J), each weighing approximately 20–25 g. rBPI$_{23}$ was dissolved in 0.5M NaCl, 20mM sodium acetate, pH 6.0 and diluted with PBS buffer (1 mg/ml) for administration at 0.125 mg/mouse. Thaumatin protein in PBS (0.121 mg/mouse) or PBS buffer alone (0.1 ml) were administered as controls.

Figure 7:
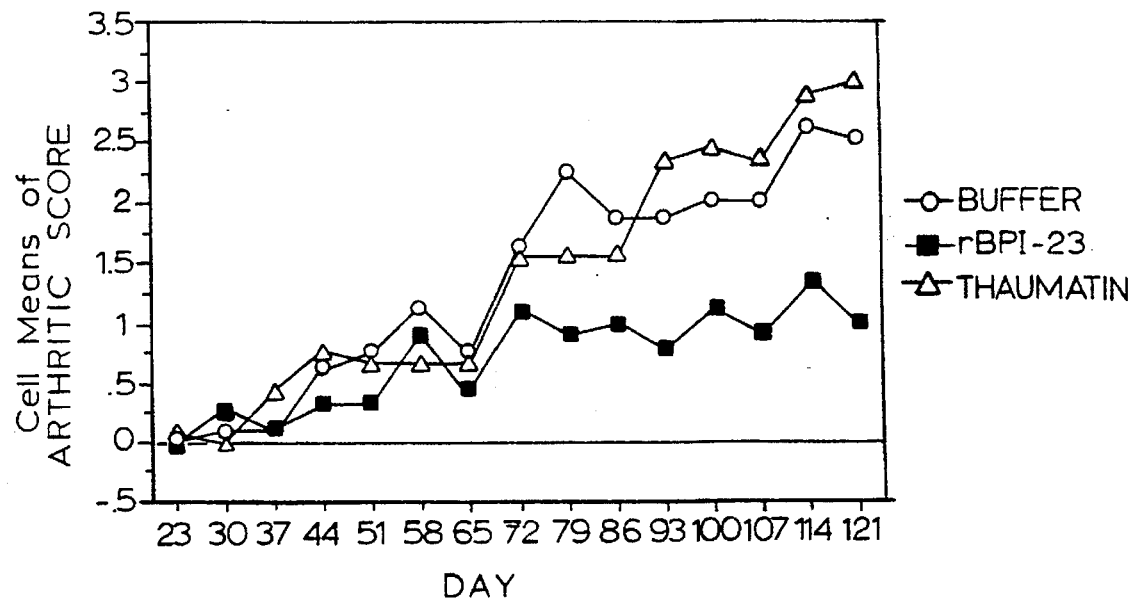
FIG. 7 depicts a graph showing the effect of $rBPI_{23}$ and thaumatin control protein on arthritic scores in a collagen-induced arthritis model with mild arthritis.

The results shown in FIG. 7 demonstrate that the rBPI$_{23}$ has a statistically significant effect in reducing the arthritic score of treated mice compared with the PBS buffer and thaumatin protein controls.

EXAMPLE 8

THERAPEUTIC EFFECTS OF BPI PROTEIN PRODUCTS IN COMPARISON WITH PROTAMINE SULFATE FOR CHRONIC INFLAMMATORY DISEASE: COLLAGEN INDUCED ARTHRITIS MODEL

Figure 8:
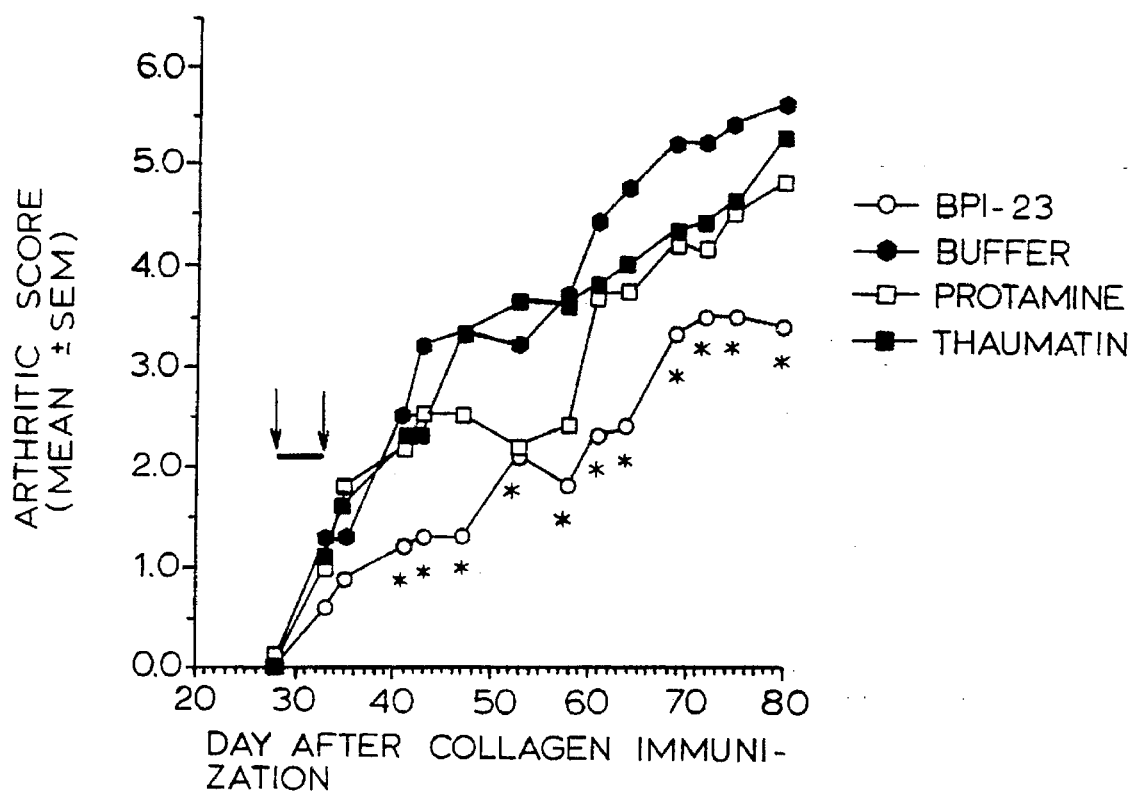
FIG. 8 depicts a graph showing the effect of $rBPI_{23}$ and protamine on arthritic scores in a collagen-induced arthritis model with severe arthritis.

The collagen-induced arthritis model of Example 7 was used to evaluate the performance of a BPI protein product in comparison with prommine sulfate, using both thaumatin protein and buffer as controls. Specifically, rBPI$_{23}$ a was dissolved in 0.5M NaCl, 20 mM sodium acetate, pH 6.0 and diluted with PBS buffer (1 mg/ml) and was administered at 0.125 mg/mouse. The other test materials were administered at the following dosages: protamine sulfate (Sigma Chemical Co) (0.13 mg/mouse), thaumatin (0.121 mg/mouse), and PBS buffer (0.1 ml). Each of four groups of ten mice received test or control materials through intravenous injection via the tail vein on each of days 28 through 32. FIG. 8 discloses the results of arthritic scores for the various treatment and control protocols evaluated at days 28–80. The stars (*) in FIG. 8 represent a statistically significant difference between rBPI$_2$ and buffer at p<0.01 while the pluses (+) represent a statistically significant difference between rBPI$_{23}$ and buffer at p<0.05. These results show that the rBPI$_{23}$ significantly reduced arthritic score for mice treated in the model system.

EXAMPLE 9

GRAM-NEGATIVE INDUCED REACTIVE ARTHRITIS MODELS

Figure 9:
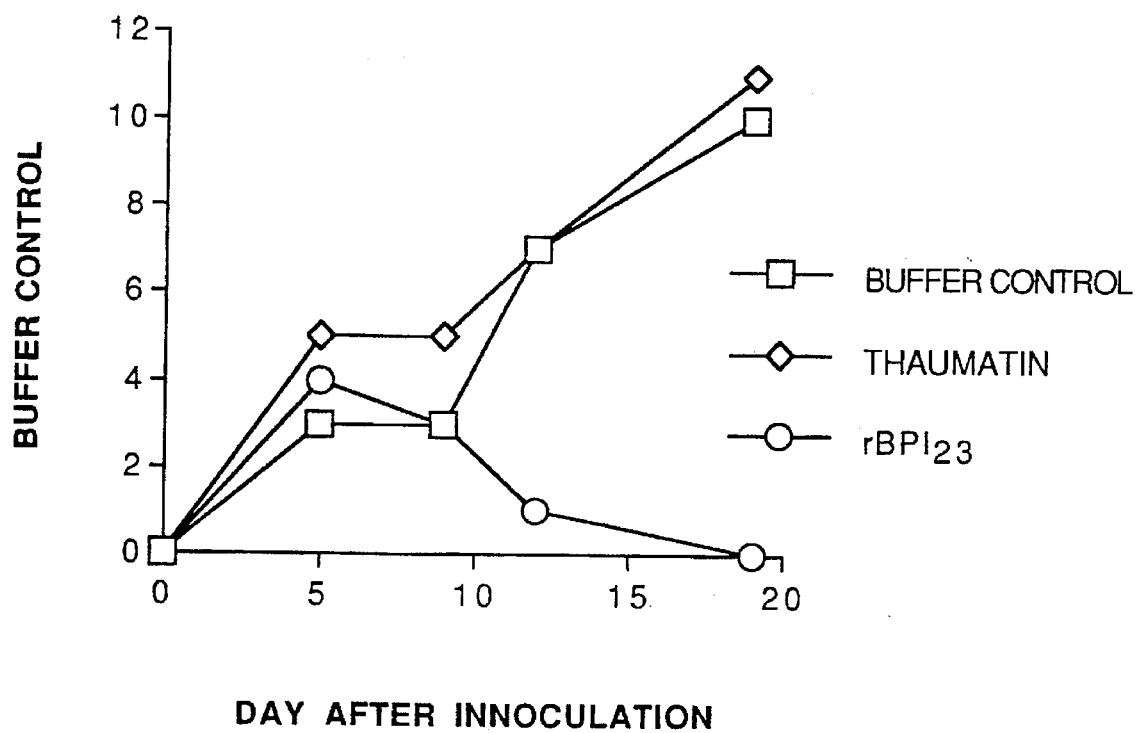
FIG. 9 depicts a graph showing the effect of $rBPI_{23}$ on the incidence of arthritis in a Yersinia-induced arthritis model.

The effect of administration of BPI protein products to treat reactive arthritis was studied in a *Yersinia enterocolitica* reactive arthritis model according to the method of Yong et al., *Microbial Pathogenesis*, 4:305–310 (1988). Specifically, BPI protein products are administered to DBA/2J male mice which had previously been injected intravenously through the tail vein with *Yersinia enterocolitica* cWA 0:8 T2 (i.e., lacking the virulence plasmid according to Yong et al. supra) at a dosage of 4×10$^8$ bacteria calculated to induce a non-septic arthritis in the mice. Each of three groups of 15 mice each received test or control materials through intravenous injection via the tail vein. The mice were given either rBPI$_{23}$ at a dosage of about 5.0 mg/kg dissolved in a buffer of 20 mM sodium citrate, 150 mM sodium chloride, 0.1% poloxamer 188, 0.002% polysorbate 80, pH 5.0; thaumatin protein at a dosage of about 5.0 mg/kg dissolved in the buffer of 20 mM sodium citrate, 150 mM sodium chloride, 0.1% poloxamer 188, 0.002 % polysorbate 80, pH 5.0; or the buffer alone. The results depicted in FIG. 9 show that the BPI protein product significantly reduced the incidence of reactive arthritis versus the buffer or thaumatin control protein.

Figure 10:
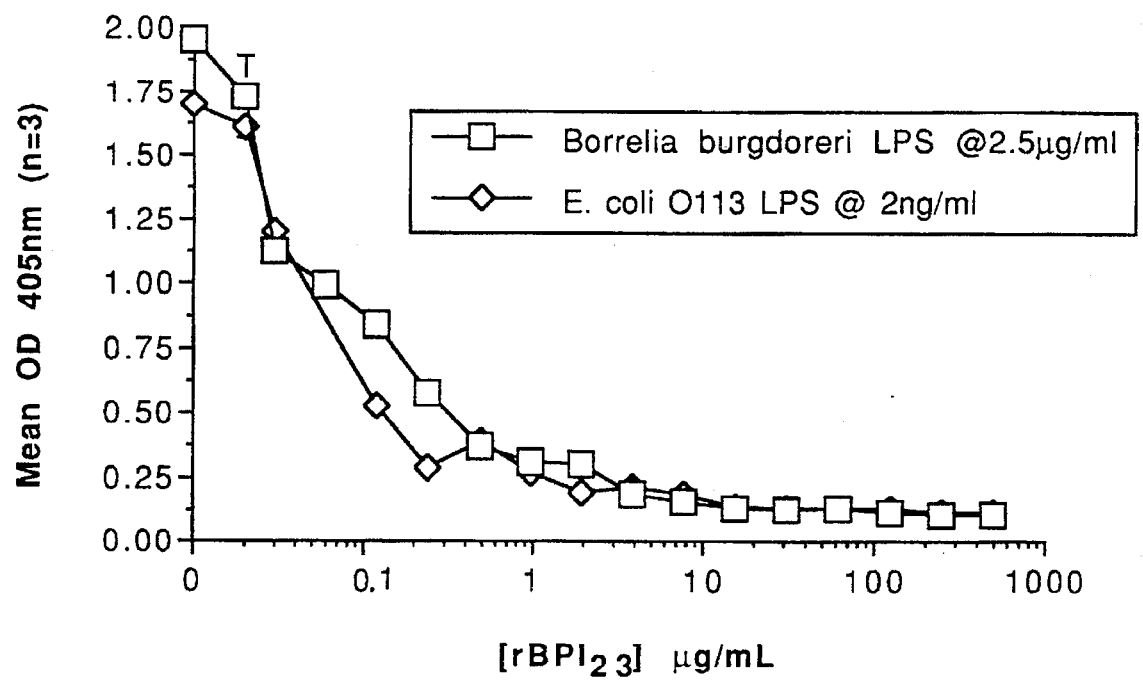
FIG. 10 depicts a graph showing the effect of $rBPI_{23}$ on inhibition of $Borrelia\ burgdorferi$ LPS-like stimulation of the LAL assay.

*Borrelia burgdorferi* is the pathogen responsible for Lyme Disease and associated arthritis and it possesses an LPS-like complex on its cell walls which is different from but structurally related to that of *E. coli*. The effect of administration of BPI protein products on inhibition of *Borrelia burgdorferi* LPS in a Limulus Amoebocyte Lysate (LAL) inhibition assay was determined. Specifically, an LAL assay according to the method of Example 15 was conducted measuring the effect of rBPI$_{23}$ on *Borrelia burgdorferi* LPS administered at 2.5 μg/mL and *E. coli* 0113 LPS administered at 2 ng/mL. The results depicted in FIG. 10 show that rBPI$_{23}$ neutralizes the effects of both *Borrelia burgdorferi* LPS and *E. coli* 0113 LPS in the LAL assay.

EXAMPLE 10

EFFECT OF BPI IN A MOUSE MALIGNANT MELANOMA MODEL

According to this example, a BPI protein product, protamine, and both thaumatin protein and buffer controls were tested for efficacy in a mouse malignant melanoma metastasis model. Specifically, four groups of nine C57BL/6J mice were inoculated with 10$^5$ B16.F10 malignant melanoma cells via intravenous injection into the tail vein on day 0. Either rBPI$_{23}$ (0.13 mg/mouse), protamine sulfate (0.13 mg/mouse), thaumatin (0.13 mg/mouse) or PBS buffer (0.1 ml/mouse) were intravenously administered into the tail vein of the mice on days 1, 3, 6, 8, 10, 13, 15, 17, and 19. The animals were sacrificed via cervical dislocation on Day 20 for observation of lung tissues. The lobes of each lung were perfused and inflated by injecting 3 ml water into the lung via the trachea. Superficial tumor nodules were then counted with the aid of a dissecting microscope and the number of tumors found per group analyzed for statistically significant differences. While the data was not statistically significant, animals treated with BPI$_{23}$ had the lowest tumor load, followed by those treated with protamine, the thaumatin protein control and the buffer control. The lack of statistical significance (tumor number did not adequately reflect tumor size) indicated that a more specific assay methodology would be needed to determine the tumor load.

EXAMPLE 11

EFFECT OF BPI IN A MOUSE MALIGNANT MELANOMA MODEL

A BPI protein product, protamine, and both thaumatin protein and buffer controls were again tested for efficacy in the mouse malignant melanoma metastasis model of Example 10. Specifically, six groups of C57BL/6J mice were inoculated with 10$^5$ B16.F10 malignant melanoma cells via intravenous injection into the tail vein on day 0. Either rBPI$_{23}$ (0.125 mg/mouse), protamine sulfate (0.125 mg/mouse), thaumatin (0.125 mg/mouse) or PBS buffer as set out in Table 2 below were intravenously administered into the tail vein of the mice on days 1, 2, 5, 7, 9, 12, 14, 16, and 19. All animals in groups A-D were sacrificed by cervical dislocation on day 20 for observation of lung tissues. The lungs were removed and placed into a beaker of cold water. The lobes of each lung were then perfused and inflated by injecting 3 ml of water into the lung via the trachea. Superficial tumor nodules are then analyzed for melanin content.

TABLE 2

| Group | Control/Test Article | No. of Animals |
|---|---|---|
| A | Buffer | 10 |
| B | Protamine | 10 |
| c | Thaumatin | 10 |
| D | rBPI$_{23}$ | 10 |
| E | Buffer | 5 |
| F | rBPI$_{23}$ | 5 |

Figure 11:
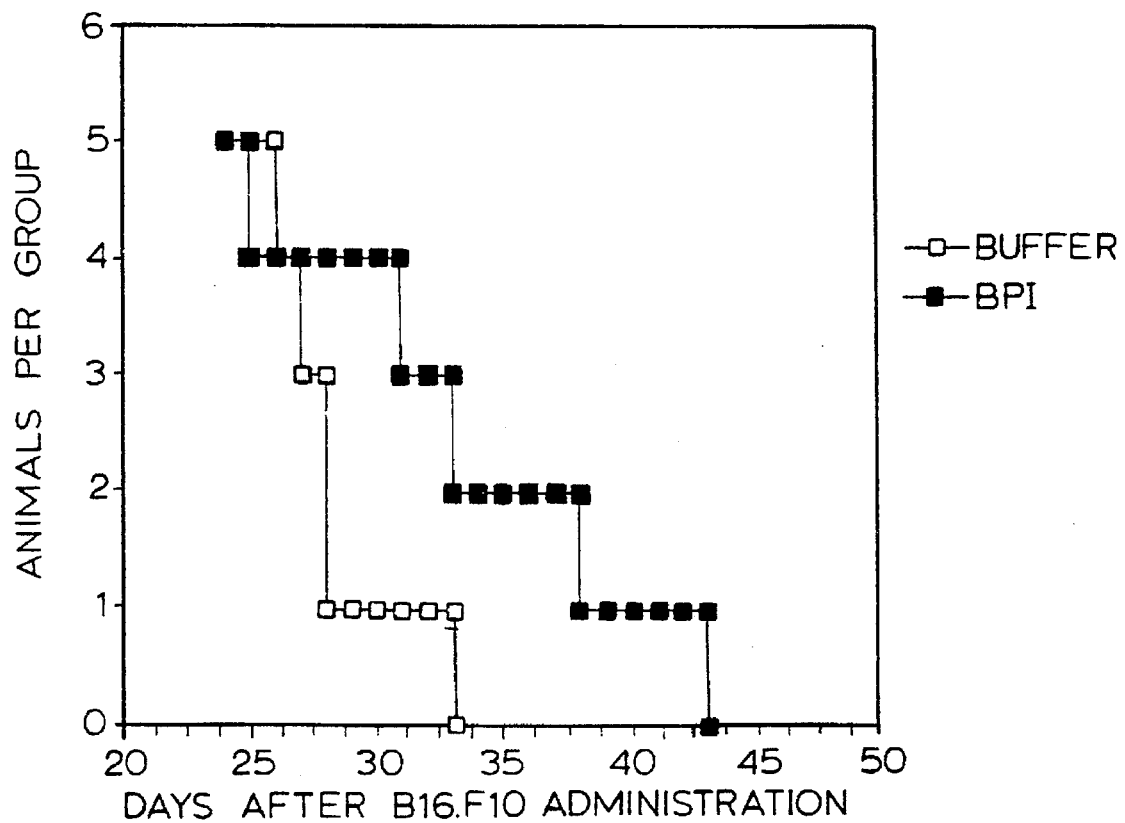
FIG. 11 depicts a graph showing survival of mice treated with BPI or a buffer in a mouse melanoma metastasis model.

Groups E and F comprising animals treated with either buffer or rBPI$_{23}$ respectively were not sacrificed but were observed once daily for mortality. FIG. 11 shows the survival data for the two groups of animals. Although all ten of the animals had died by day 43, the BPI treated mice generally survived significantly longer than the untreated mice indicating that BPI had an anti-angiogenic effect and slowed metastasis of the melanoma tumors.

Given the above, according to an additional aspect of the invention, BPI protein products may be used to inhibit Kaposi's Sarcoma in a model system such as that of Miles et al., VII International Conference on AIDS, Florence, Italy, Paper 41(8), 1991.

EXAMPLE 12

EFFECT OF BPI ON ENDOTHELIAL CELL PROLIFERATION

Murine cerebral capillary endothelial cells (EC) as described in Bauer, *Microvascular Research* 37:148–161

(1989) were passaged in Medium 199 containing Earle's salts, L-glutamine and 2.2 g/l of sodium bicarbonate (Gibco, Grand Island, N.Y., #400-100EB), plus 10% heat inactivated fetal calf serum (Irvine Scientific, Irvine, Calif.) and 1% penicillin/streptomycin (Gibco, #600-5140AG). Harvesting of the confluent cells was performed by trypsinization with trypsin-EDTA (Gibco #610-5300PG) for 3 minutes. The trypsinization was stopped by adding 10 ml of the passage medium to the flask. Proliferation assays were performed on freshly harvested EC in standard flat bottom 96 well microtiter plates. A final volume of 200 µl/well was maintained for each well of the assay. A total of $4 \times 10^4$ EC were added to each well with varying concentrations of $rBPI_{23}$, thaumatin control protein or buffer control. After 48 hours of culture in a 5% $CO_2$ incubator, 1 µCi of [methyl-$^3$H] thymidine in 10 µl of Medium 199 was added to each well. After a 24 hour pulse, the EC cells were harvested by trypsinization onto glass microfiber filters and incorporated [$^3$H] thymidine was quantitated with a gas proportional solid phase beta counter.

Figure 12:
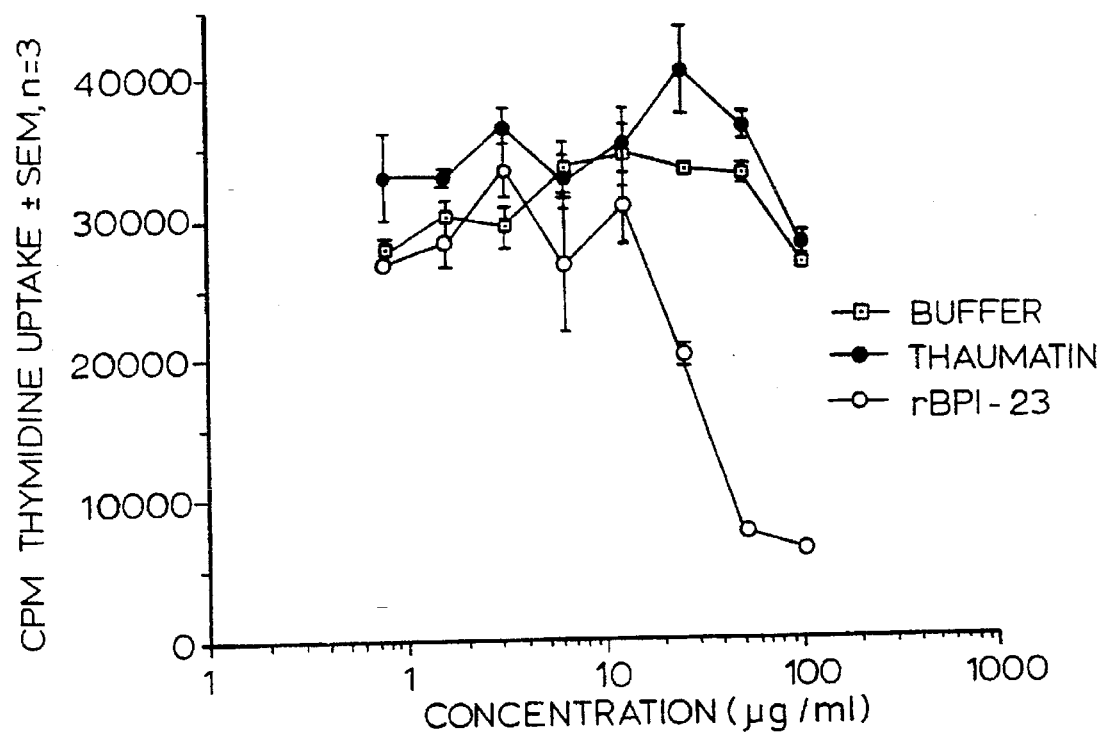
FIG. 12 depicts a graph showing the effect of $rBPI_{23}$ on Type II murine capillary endothelial cell proliferation.

Concentration dependent inhibition of EC cell proliferation by $rBPI_{23}$ is shown in FIG. 12. No effect was observed when similar concentrations of thaumatin or equal volumes of the buffer were added to the wells. The first inhibition of proliferation is observed at 12.4 µg/ml $rBPI_{23}$ and the effect appears to be maximal at 50 µg/ml. The growth of the EC cells is known to be dependent on FGF-2 (bFGF) in the calf serum and FGF-2 requires cell surface heparan for receptor activation (Yayon et al., Cell 64:841-848, 1991). Without intending to be bound by a theory of the invention, it is believed that $rBPI_{23}$ bound to cell surface heparan on the EC cells interferes with the activation of the cells by FGF-2.

Direct binding studies of $rBPI_{23}$ on the EC cells were performed by harvesting the 10× passaged cells from a confluent flask and resuspending the trypsinized cells in 12.5 ml of culture medium. 0.5 ml of the suspension was added to each well of a standard 24 well tissue culture plate and incubated overnight. The plate was washed with 0.1% bovine serum albumin in phosphate buffered saline containing calcium and magnesium. (Gibco.) After washing, 0.5 ml of the BSA/PBS was added per well. Preliminary experiments indicated that 50 ng/ml of $^{125}$I-labeled $rBPI_{23}$ added to the wells produced approximately 30,000 specific cpm after a 3 hour, 4° C. incubation with 3× washing in PBS and lysis with 1M NaOH from gamma counting of the lysate.

Figure 13:
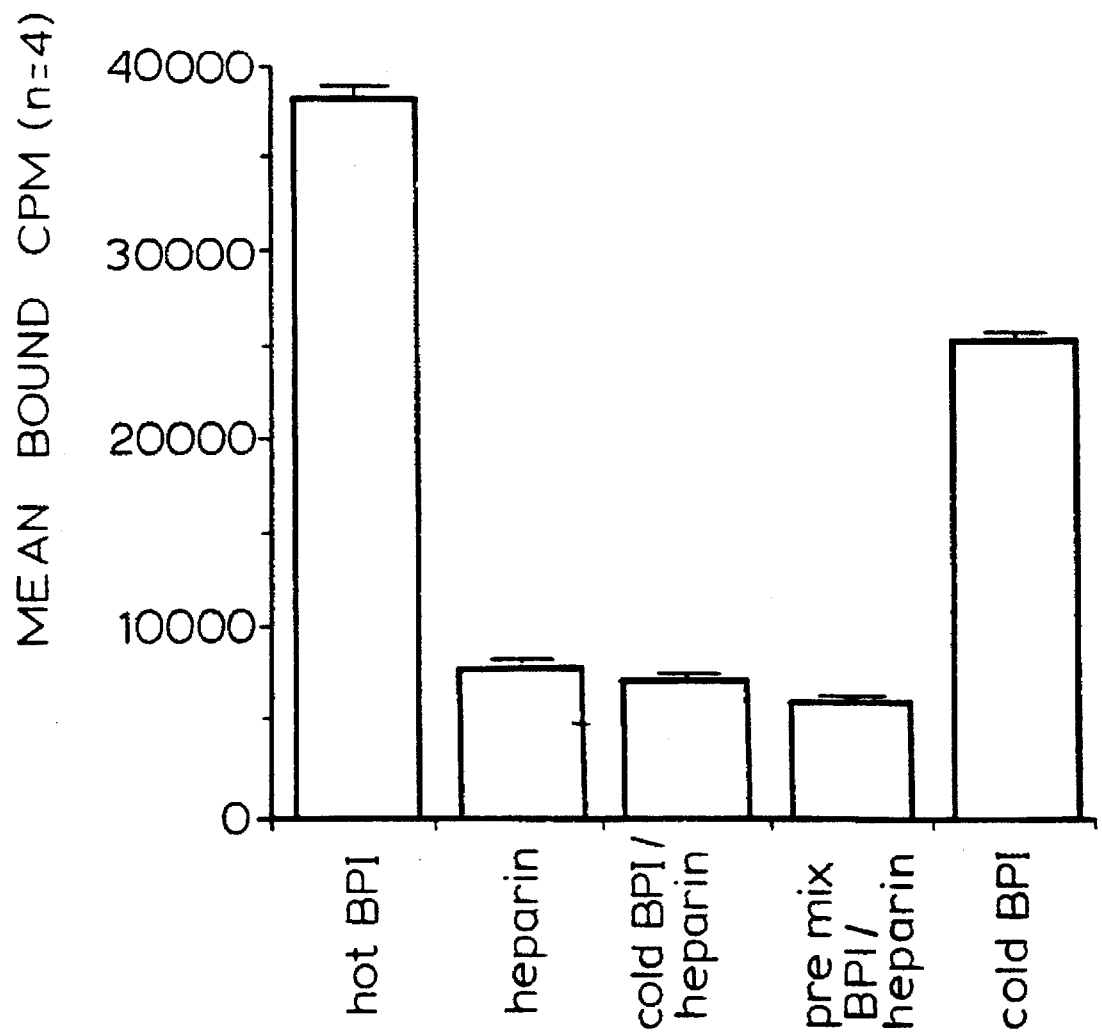
FIG. 13 illustrates BPI binding to epithelial cells.

The specific binding of 50 ng/ml $^{125}$I-labeled, "hot" $rBPI_{23}$ to the EC cells could be competed by addition of 20 µg/ml heparin (Sigma, Grade I). Similar competition was observed for unlabeled ("cold") $rBPI_{23}$ added to the binding culture. The combination of unlabeled $rBPI_{23}$ with heparin (concurrently added or pre-mixed prior to addition) could not reduce the binding below the heparin only competition (FIG. 13). These data indicate that $rBPI_{23}$ binds to endothelial cells via heparin-like molecule and that this binding appears to interfere with EC cell proliferation to a heparin binding growth factor (FGF-2).

EXAMPLE 13

PREPARATION OF 15-MER SYNTHETIC PEPTIDES OF BPI

In order to assess biological properties of peptide fragment BPI protein products, 15-mer amino acid synthetic peptides based on the 23 kD amino terminal fragment of BPI were prepared and evaluated for heparin-binding activity, activity in a Limulus Amoebocyte Lysate Inhibition (LAL) assay and bactericidal activity. Specifically, 47 synthetic peptides each comprising 15 amino acids and overlapping the adjacent peptides by 11 amino acids were prepared, in duplicate, based on the sequence of $rBPI_{23}$ described above.

Peptides were simultaneously synthesized according to the methods of Maeji et al., Immunol. Methods, 134:23–33 (1990) and Gammon et al., J. Exp. Med., 1 73:609–617 ( 1991 ), utilizing the solid-phase technology of Cambridge Research Biochemicals Ltd. under license of Coselco Mimotopes Ply Ltd. Briefly, the sequence of $rBPI_{23}$ (1–199) was divided into 47 different 15-mer peptides that progressed along the linear sequence of $rBPI_{23}$ by initiating a subsequent peptide every fifth amino acid. This peptide synthesis technology allows for the simultaneous small scale synthesis of multiple peptides on separate pins in a 96-well plate format. Thus, 94 individual pins were utilized for this synthesis and the remaining to pins (B,B) were subjected to the same steps as the other pins without the addition of activated FMOC-amino acids. Final cleavage of the 15-mer peptides from the solid-phase pin support employed an aqueous basic buffer (sodium carbonate, pH 8.3). The unique linkage to the pin undergoes a quantitative diketopiperazine cyclization under these conditions resulting in a cleaved peptide with a cyclo(lysylprolyl) moiety on the carboxyl-terminus of each peptide. The amino-termini were not acetylated so that the free amino group could potentially contribute to anion binding reactions. An average of about 15 µg of each 15-mer peptide is recovered per well.

EXAMPLE 14

HEPARIN BINDING BY 15-MER SYNTHETIC PEPTIDES OF BPI

Figure 14:
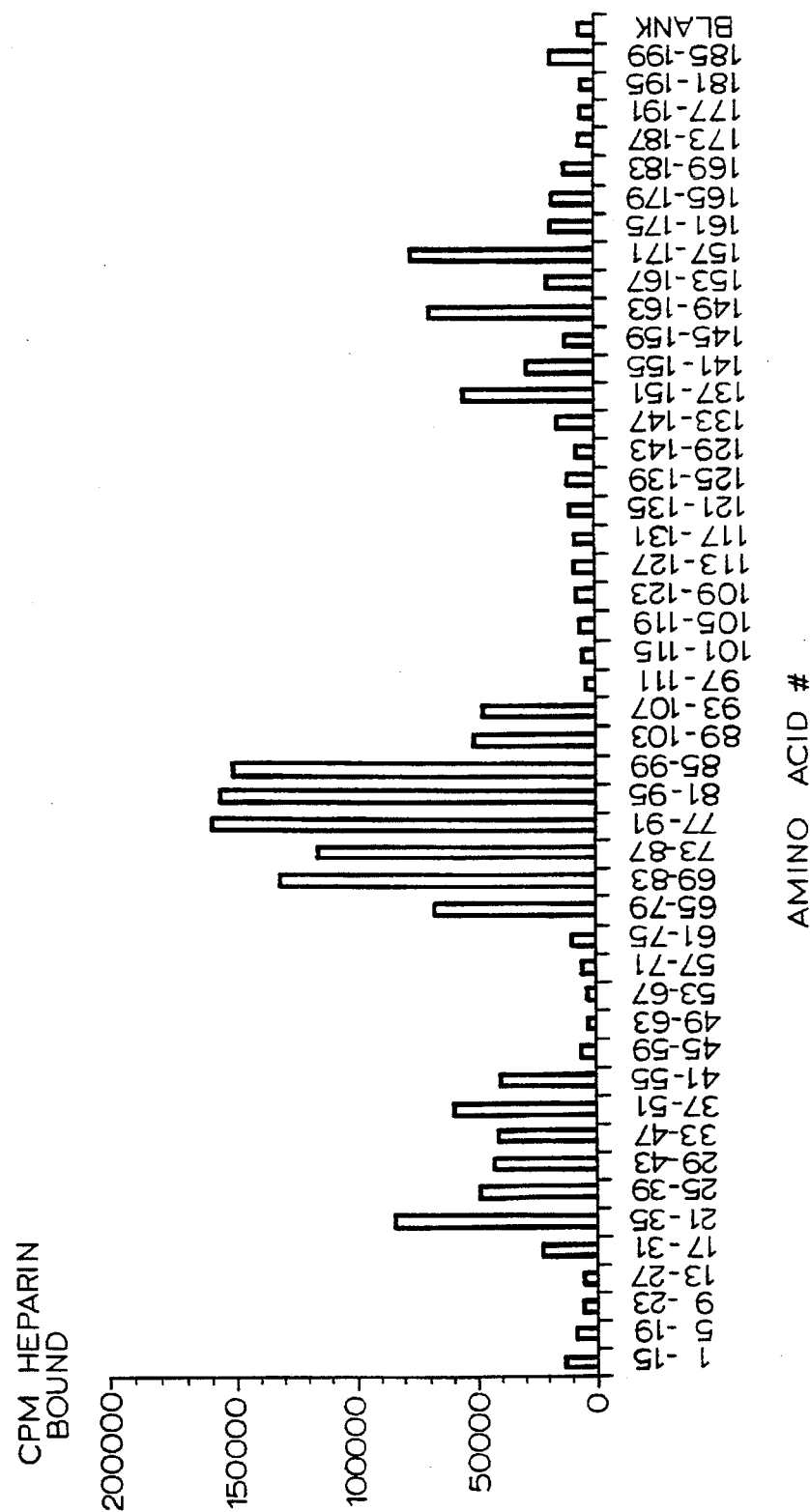
FIG. 14 depicts a graph of a heparin binding assay for synthetic BPI peptides.

The synthetic BPI protein product peptides described above were subjected to a heparin binding assay according to the methods described in Example 1. The results, as shown in FIG. 14, indicate the existence of three separate functional domains with heparin binding activity; the first extending from about amino acids 21–55; the second extending from about amino acids 65–107; and the third extending from about amino acids 137–171. Material from blank control pins had no heparin binding effects.

EXAMPLE 15

EFFECT OF 15-MER SYNTHETIC PEPTIDES OF BPI ON AN LAL ASSAY

The synthetic BPI protein product peptides were subjected to a Limulus Amoebocyte Lysate (LAL) inhibition assay to determine LPS binding properties. Specifically, the synthetic BPI peptides were mixed in Eppendorf tubes with a fixed concentration of E. coli 0113 LPS (4 ng/ml final) and incubated at 37° C. for 3 hours with occasional shaking. Addition controls comprising 0.05 µg/mL were also tested. Following incubation, 360 µl DPBS was added per tube to obtain an LPS concentration of 200 pg/mL for the LAL assay. Each sample was then transferred into Immulon II strips (Dynatech, Chantilly, Va.) in volumes of 50 µl per well.

Limulus amoebocyte Lysate (Quantitative chromogenic LAL kit, Whitaker Bioproducts, Inc., Walkersville, Md.) was added at 50 µl per well and the wells were incubated at room temperature for 25 minutes. Chromogenic substrate was then added at a volume of 100 µl per well and was well mixed. After incubation for 20 to 30 minutes at room temperature, the reaction was stopped with addition of 100 µl of 25% acetic acid. Optical density at 405 nm was then measured in a multiplate reader (Vmax, Molecular Dynamics, Menlo Park, Calif.) with the results shown in FIG. 15 in terms of percent inhibition of LPS. The data in FIG. 15 indicate at least three major domains with significant LAL inhibition; the first extending from amino acids 17–55; the second extending from about amino acids 73–99 and the third extending from about amino acids 137–163. Other individual peptides also exhibit LAL inhibition. In contrast, material from blank control pins did not exhibit LPS neutralizing effects as measured by the LAL assay.

EXAMPLE 16

BACTERICIDAL EFFECTS OF 15-MER SYNTHETIC PEPTIDES OF BPI

The synthetic BPI protein product peptides were tested for bactericidal effects against the rough mutant *E. coli* J5 bacteria in a radial diffusion assay. Specifically, an overnight culture of *E. coli* J5 was diluted 1:50 into fresh tryptic soy broth and incubated for 3 hours at 37° C. to attain log phase. Bacteria were then pelleted at 3,000 rpm for 5 minutes in a Sorvall RT6000B. 5 mL of 10 mM sodium phosphate buffer (pH 7.4) was added and the preparation was re-centrifuged. The supernatant was decanted and 5 mL of fresh buffer was added, the bacteria were resuspended and their concentration was determined by measurement of absorbance at 590 nm. Absorbance of $1.25 \times 10^9$ CFU/mL suspension equals 1.00. The bacteria were diluted to $4 \times 10^6$ CFU/mL in 10 mL of molten underlayer agarose (approximately 45° C.) and inverted repeatedly to mix with 15 mL polypropylene tubes used for this purpose.

The entire contents of the tube were poured into a perfectly level square petri dish and distributed evenly by rocking the dish side to side. The agarose hardened in less than 30 seconds and had a uniform thickness of about 1 mm. A series of wells were then punched into the hardened agarose using a sterile 3 mm punch attached to a vacuum apparatus. The punch was sterilized with 100% alcohol and allowed to air dry.

10 μL of the synthetic BPI peptides were carefully pipetted into each well. As controls, pH 8.3 buffer was added to a separate well (as positive controls, 5 μg/mL and 1 μg/mL concentration of rBPI$_{23}$ was also added. In addition, products from the blank pins B and B were tested as controls. The plate was allowed to incubate at 37° C. for 3 hours and 10 mL of molten overlayer agarose (at approximately 45° C.) was then added into the level petri dish, allowed to harden and incubated overnight at 37° C. A clear zone was seen against the lawn of bacteria in those wells having bactericidal activity. In order to visually enhance this zone, a dilute Coomassie solution (0.002% Coomassie Brilliant Blue, 27% methanol, 15% formaldehyde (37% stock solution) and H$_2$O) was poured over the agar and allowed to stain for 24 hours. The bacterial zones were measured with a Mitutoyo micrometer.

Figure 16:
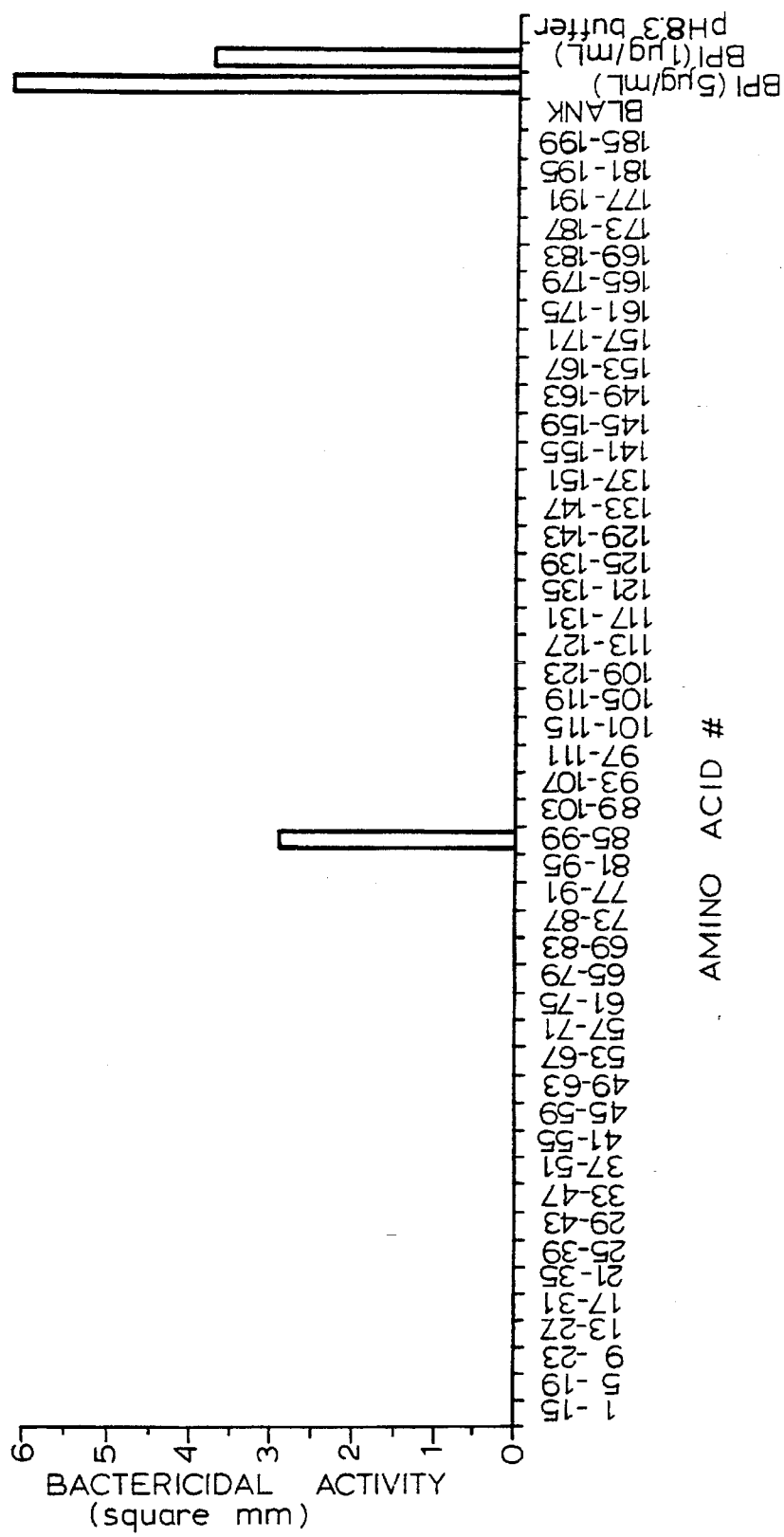
FIG. 16 depicts a graph of a radial diffusion bactericidal assay for synthetic BPI peptides.

The results of the assay are shown in FIG. 16 where the only synthetic BPI peptide seen to have bactericidal activity was a fragment corresponding to amino acids 85–99. The positive rBPI$_{23}$ controls also had bactericidal effects while the buffer and blank pin controls did not.

EXAMPLE 17

PREPARATION OF BPI PEPTIDE FRAGMENTS

Based on the results of testing of overlapping peptides in Examples 13 through 16, BPI protein product peptide fragments were prepared by solid phase peptide synthesis according to the methods of Merrifield, *J. Am. Chem. Soc.* 85:2149 (1963) and Merrifield et al., *Anal. Chem.* 38:1905–1914 (1966) using an Applied Biosystems, Inc. Model 432 synthesizer. Nine BPI protein product peptides designated BPI-2 through BPI-10 were prepared having the amino acid sequences of portions of amino acid residues 1–199 of rBPI$_{23}$ as set out in Table 3 below. In the cases of BPI-7, BPI-9 and BPI-10 the peptides represented partial or even multiple repeats of sequence. Specifically, BPI-7 comprises a 20-mer consisting of amino acid residues 90–99 repeated twice in a single linear chain. BPI-10 comprises a 30-mer consisting of amino acid residues 90–99 repeated three times in a single linear chain. BPI-9 comprises a 16-mer comprising amino acid residues 94–99 followed by residues 90–99 in a single linear chain.

TABLE 3

| BPI Protein Product Peptides | | | |
|---|---|---|---|
| Polypeptide No. | Amino Acid Region | Amino Acid Residues | MW (daltons) |
| BPI-2 | 85–99 | 15 | 1828.16 |
| BPI-3 | 73–99 | 27 | 3072.77 |
| BPI-4 | 25–46 | 22 | 2696.51 |
| BPI-5 | 142–163 | 22 | 2621.52 |
| BPI-6 | 112–127 | 16 | 1569.82 |
| BPI-7 | 90–99, 90–99 | 20 | 2644.66 |
| BPI-8 | 90–99 | 10 | 1316.8 |
| BPI-9 | 94–99, 90–99 | 16 | 2131.34 |
| BPI-10 | 90–99, 90–99, 90,99 | 30 | 3958.45 |

EXAMPLE 18

HEPARIN BINDING BY BPI PROTEIN PRODUCT PEPTIDES

Figure 17:
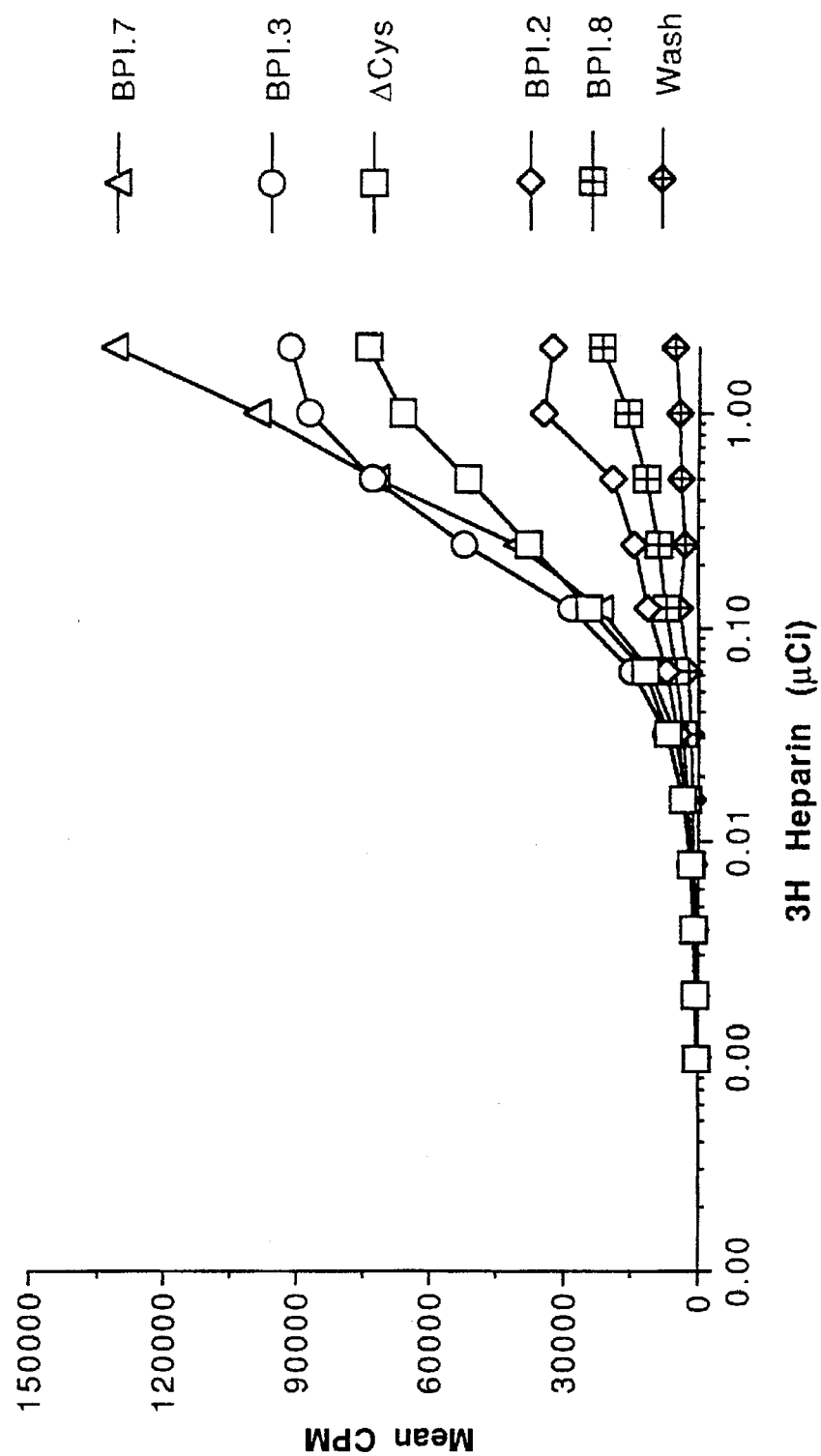
FIG. 17 depicts a graph showing the effect of synthetic BPI peptides in a heparin binding assay.

In this example BPI protein product peptides BPI-2, BPI-3, BPI-4, BPI-6, BPI-7, and BPI-8 along with BPI cys were subjected to a heparin binding assay according to the methods described in Example 1. The results, as shown in FIG. 17 indicate that BPI-7, and BPI-8 have extremely high heparin binding capacity while BPI-2 and BPI-3 have more moderate heparin binding capacity and BPI-4 and BPI-6 have little or no heparin binding capacity.

EXAMPLE 19

HEPARIN NEUTRALIZATION BY BPI PROTEIN PRODUCT PEPTIDES

Figure 18A:
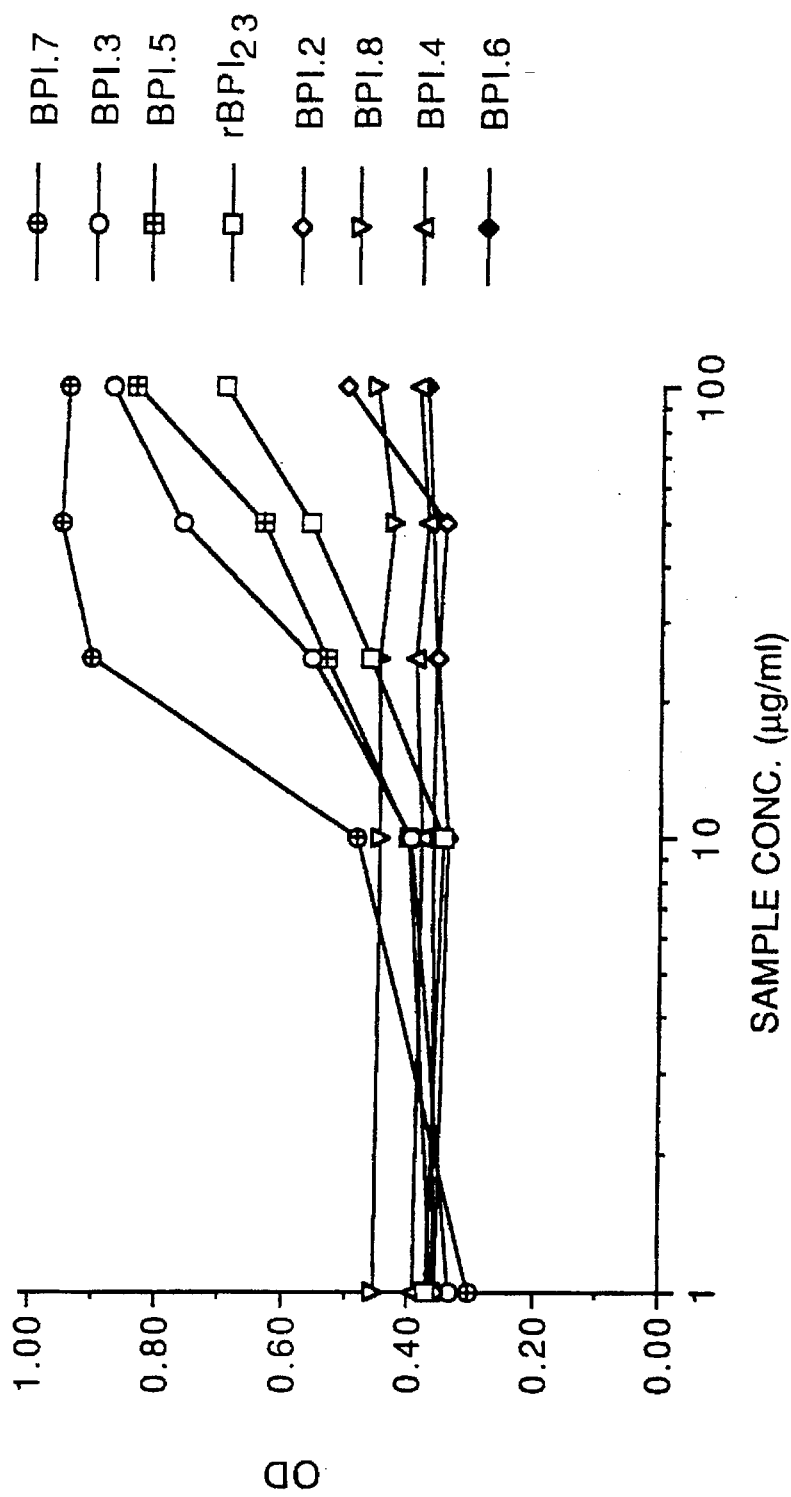
FIGS. 18a and 18b depict graphs showing the effect of synthetic BPI peptides on ATIII heparin inhibition of thrombin.
Figure 18B:
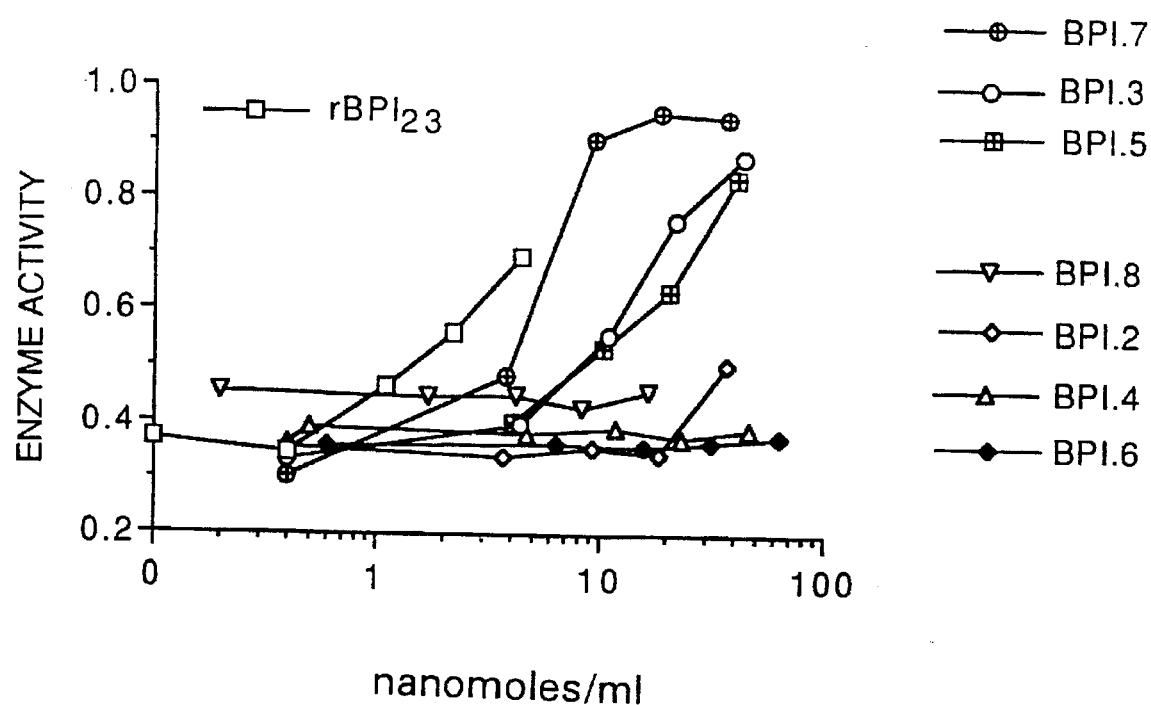

In this example BPI protein product peptides BPI-2, BPI-3, BPI4, BPI-5, BPI-6, BPI-7, and BPI-8 along with rBPI$_{23}$ were subjected to an assay to determine their effect on thrombin inactivation by ATIII/heparin complexes according to the method of Example 3. Varying concentrations of the BPI protein products ranging from 1.0 μg/mL to 100 μg/mL were administered to determine their effect. BPI protein peptides BPI-7, BPI-3, and BPI-5 each had the most significant heparin neutralization effects as shown in FIGS. 18a and 18b which depict the sample concentrations as weight or molar concentrations respectively.

EXAMPLE 20

EFFECT OF BPI PROTEIN PRODUCT PEPTIDES ON AN LAL ASSAY

Figure 19A:
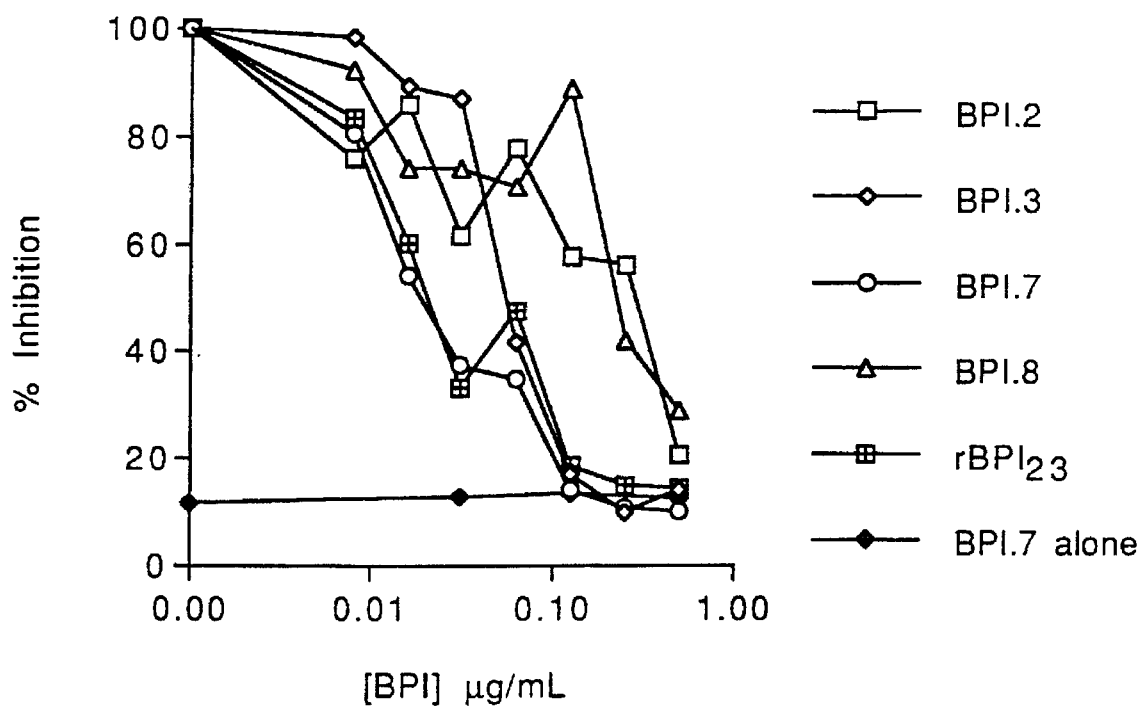
FIGS. 19a and 19b depict graphs showing the effect of synthetic BPI peptides in an LAL inhibition assay.
Figure 19B:
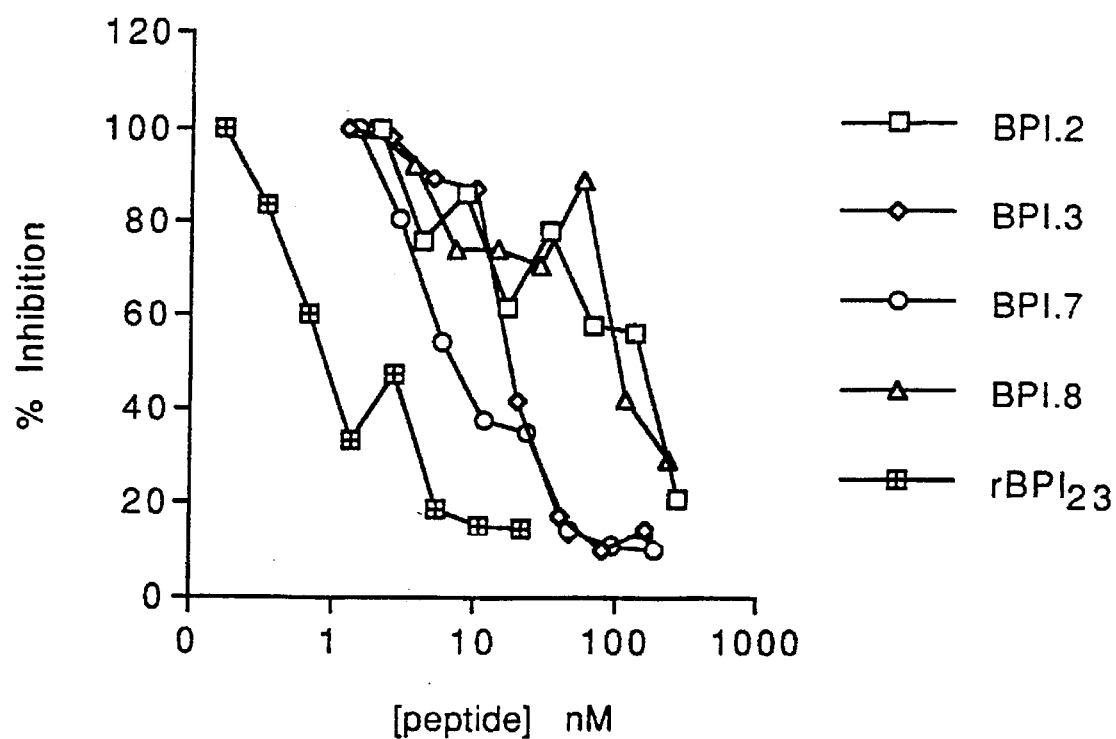

In this example BPI protein product peptides BPI-2, BPI-3, BPI4, BPI-6, BPI-7, and BPI-8 along with rBPI$_{23}$ were subjected to an LAL assay according to the method of Example 15 to determine their LPS binding and inhibition properties. The results show that BPI-7 and BPI-3 had significant LPS inhibition properties, that BPI-2 and BPI-8 had moderate LPS inhibition properties and that BPI-4 and BPI-6 had no significant LPS inhibition activity as depicted in FIGS. 19a and 19b which depict the sample concentrations as weight or molar concentrations respectively.

EXAMPLE 21

BPI PROTEIN PRODUCT PEPTIDE BACTERICIDAL ASSAY

In this example, BPI protein product peptides BPI-2, BPI-3, BPI-4, BPI-5, BPI-6, BPI-7, BPI-8, BPI-9 and BPI-10 along with rBPI$_{23}$ were tested for bactericidal effects against mutant E. coli J5 (rough) and E. coli 0111:B4 (smooth) bacteria in a radial diffusion assay according to the methods of Example 16. The results depicted in FIGS. 20a–20d show that each of BPI-2, BPI-3, BPI-5, BPI-7, BPI-8, BPI-9 and BPI-10 have greater or lesser degrees of bactericidal activity while BPI-4 and BPI-6 exhibited no bactericidal activity. The bactericidal peptides each tended to be more effective against the rough than the smooth E. coli strain.

Figure 20A:
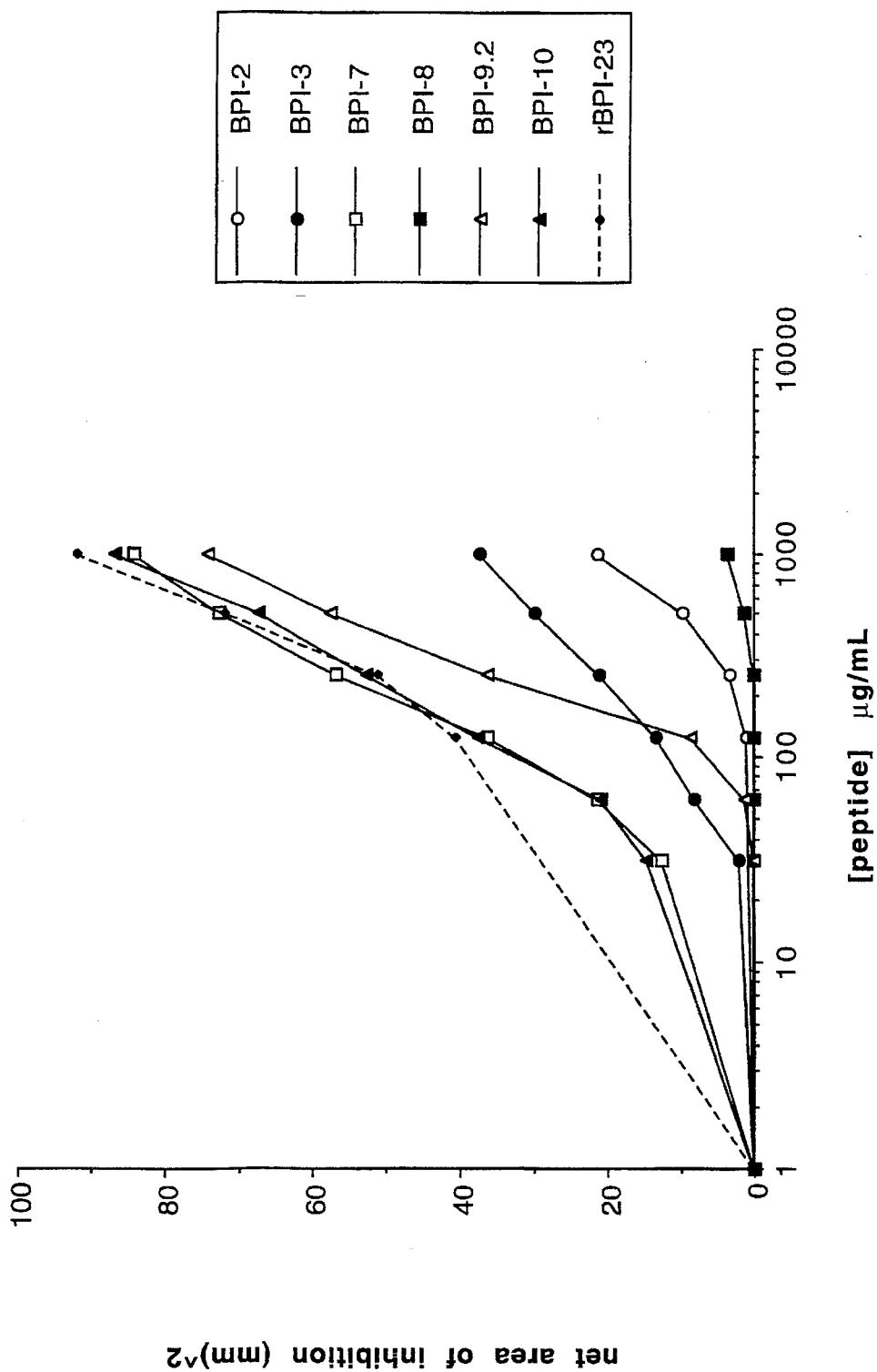
FIGS. 20a, 20b, 20c, and 20d depict graphs showing the effect of synthetic BPI peptides in radial diffusion bactericidal assays.
Figure 20B:
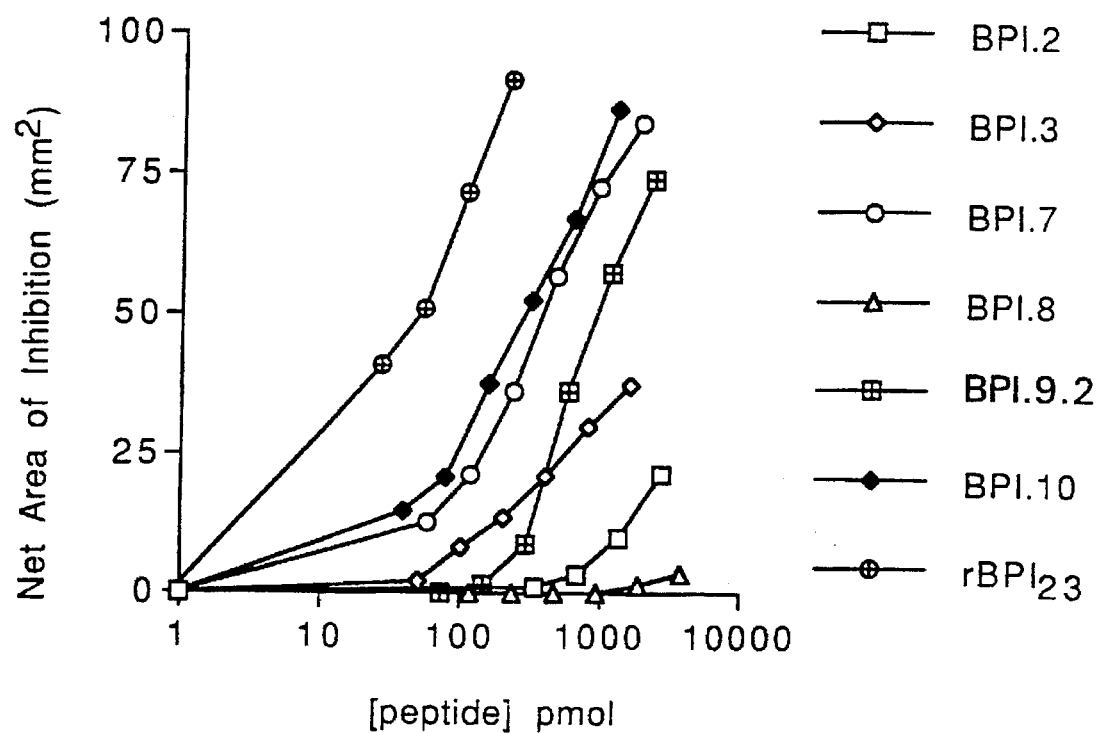
Figure 20C:
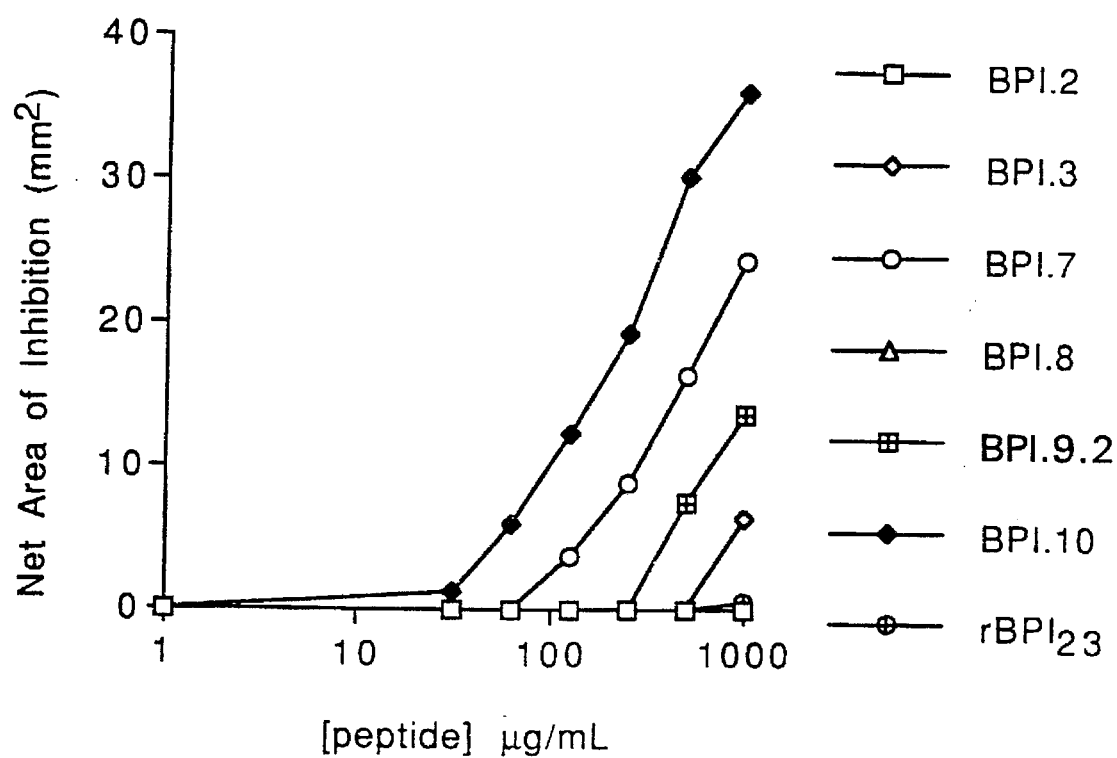
Figure 20D:
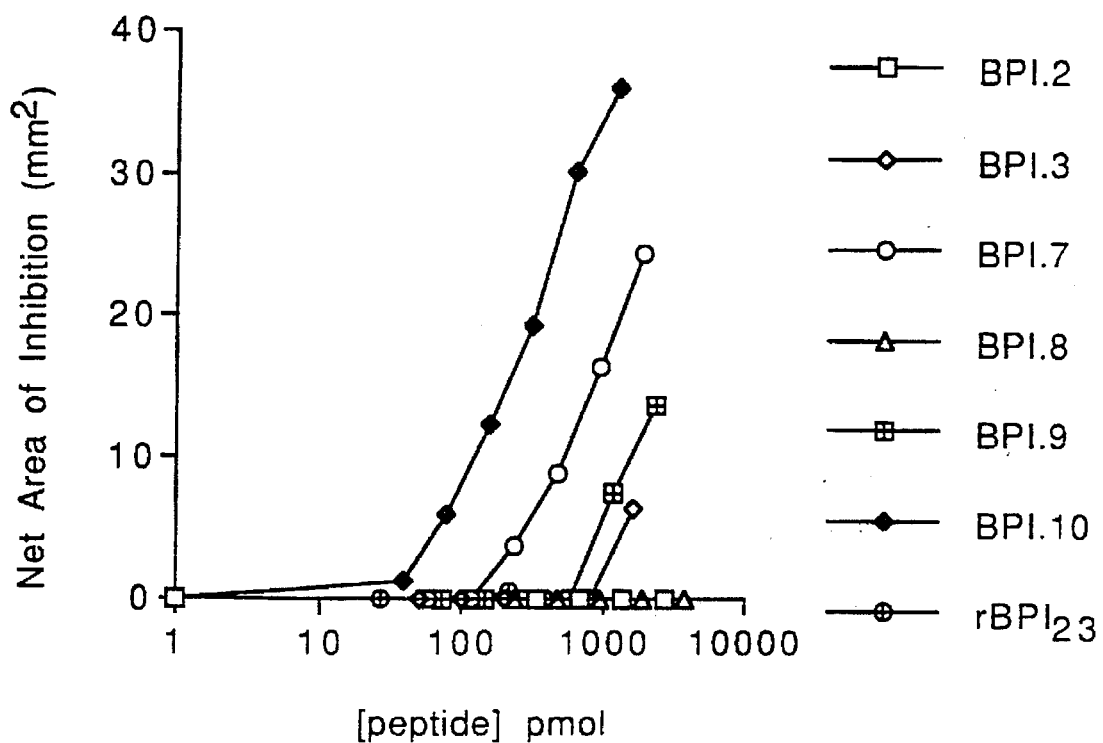
Figure 20E:
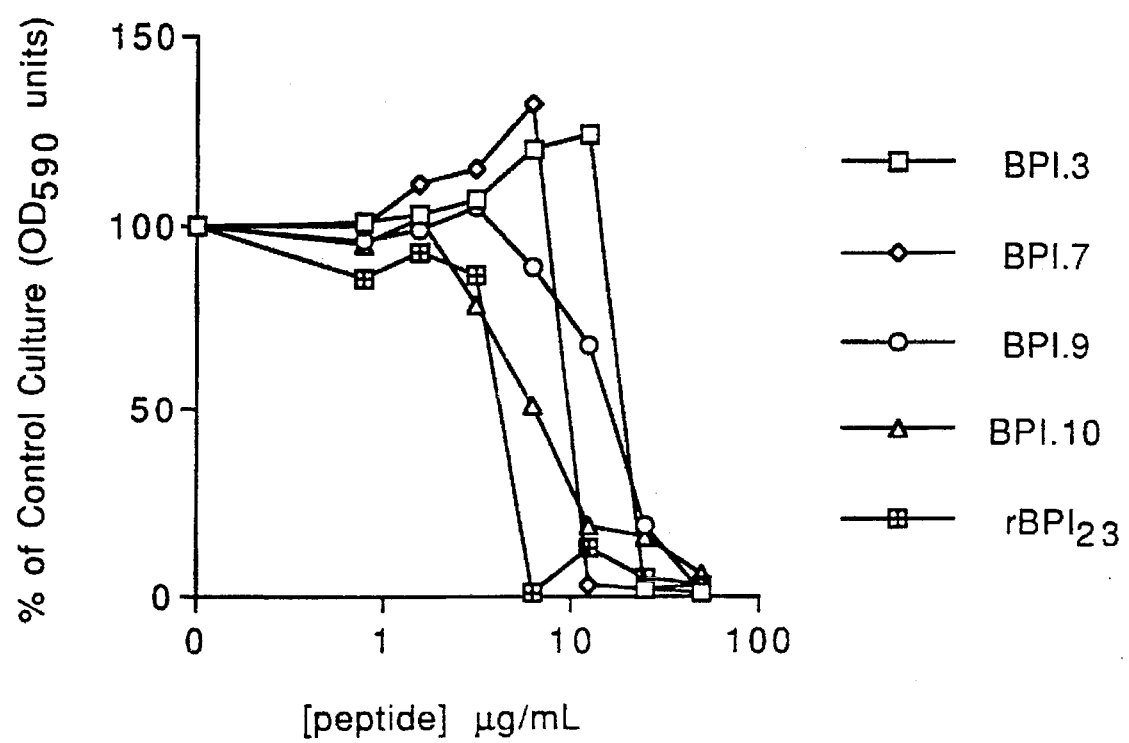
FIGS. 20e and 20f depict graphs showing the effect of synthetic BPI peptides in $E.\ coli$ broth assays.
Figure 20F:
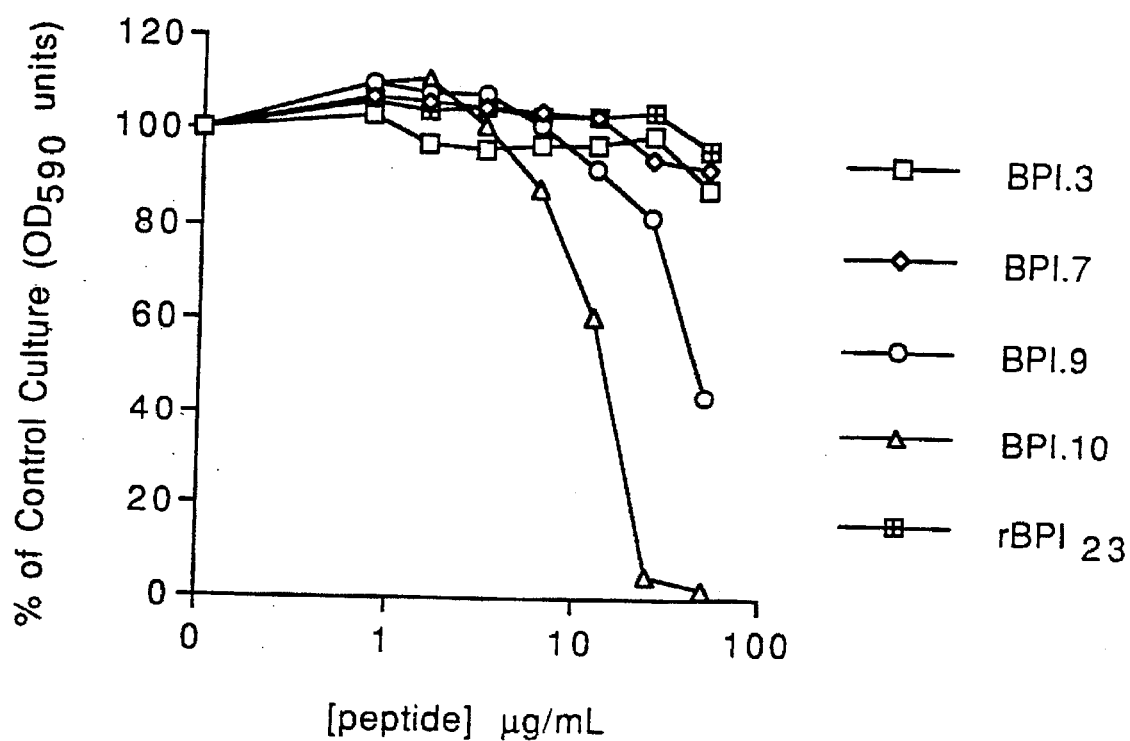

As a further aspect of this example, broth antibacterial assays were conducted to determine the bactericidal activity of certain of the BPI peptides. Specifically either E. coli J5 (rough) and E. coli 0111:B4 (smooth) bacteria were selected from single colonies on agar plates and used to inoculate culture plates to which were added serial ten-fold dilutions of the BPI protein product peptides. The plates were incubated overnight and read on an ELISA plate reader to determine the surviving colony forming units. The results of this assay are depicted in FIGS. 20e (E. coli J5) and 20f (E. coli 0111:B4) which show that BPI protein product peptides BPI-3, BPI-7, BPI-9 and BPI-10 have significant antibacterial activity.

The results of these bactericidal assays along with the heparin binding and LAL assays indicate that there exist small synthetic BPI peptides with one or more of bactericidal, heparin binding and LPS neutralizing effects and that there exist at least three distinct separate functional domains within the 23 kD amino terminal fragment. One domain resides between amino acid residues 17 and 45. A second, the most active domain, characterized by activity in all three assays, resides between amino acids 71 and 99. One specific peptide 86–99 demonstrated activity in all three assays. A third domain is composed of residues 142–169.

EXAMPLE 22

PREPARATION OF BPI PROTEOLYTIC FRAGMENT PEPTIDES

In this example chemical cleavage and enzymatic digestion processes were applied to rBPI$_{23}$, produced according to the procedures of Gazzano-Santoro et al., supra, to develop variously sized proteolytic fragments of the recombinant protein.

The rBPI$_{23}$ was reduced and alkylated prior to proteolysis by cyanogen bromide (CNBr) or endoproteinase Asp-N. The protein was desalted by cold (4° C.) acetone precipitation (1:1 v/v) overnight and pelleted by centrifugation (5000 ×g) for 10 minutes. The rBPI$_{23}$ pellet was washed twice with cold acetone and dried under a stream of nitrogen. The rBPI$_{23}$ was then reconstituted to 1 mg/ml in 8M urea/0.1M Tris, pH 8.1 and reduced by addition of 3.4 mM dithiothreitol (Calbiochem, San Diego, Calif.) for 90 minutes at 37° C. Alkylation was performed by the addition of iodoacetamide (Sigma Chemical Co., St. Louis, Mo.) to a final concentration of 5.3 millimolar for 30 minutes in the dark at room temperature. The reduced and alkylated protein was acetone precipitated, centrifuged and washed as described above and the pellet was redissolved for either CNBr or Asp-N digestion.

Prior to CNBr addition, the washed pellet was dissolved in 70% trifluoroacetic acid (TFA) (protein sequencing grade, Sigma) to a final protein concentration of 5 mg/ml. Cyanogen bromide (Baker Analyzed Reagent, VWR Scientific, San Francisco, Calif.) dissolved in 70% TFA was added to give a final 2:1 ratio of CNBr to protein (w/w). This is approximately a 75 fold molar excess of CNBr over methionine residues in the protein. The reaction was purged with nitrogen and allowed to proceed for 24 hours in the dark at room temperature. The reaction was terminated by adding 9 volumes of distilled water, and followed by freezing (−70° C.) and lyophilization.

The reduced and alkylated rBPI$_{23}$ was solubilized at 5.0 mg/ml in 8M urea/0.1M Tris, pH 8.1. An equal volume of 0.1M Tris, pH 8.1 was added so that the final conditions were 2.5 mg/ml protein in 5M urea/0.1M Tris, pH 8.1. Endoproteinase Asp-N from Pseudomonas fragi (Boehringer-Mannheim, Indianapolis, Ind.) was added at a 1:1000 (w/w) enzyme:substrate ratio and the digest was allowed to proceed for 6 hours at 37° C. The reaction was terminated by addition of TFA to a final concentration of 0.1% and the samples were then fractionated by reverse phase HPLC.

The CNBr and Asp-N fragment mixtures were purified on a Zorbax Protein Plus C$_3$ column (4.6×250 mm, 300 Å pore size, MACMOD Analytical Inc, Chadsford, Pa.). A gradient from 5% acetonitrile in 0.1% TFA to 80% acetonitrile in 0.1% TFA was run over 2 hours at 1.0 ml/min. Fragment elution was monitored at 220 nm using a Beckman System Gold HPLC. The column heating compartment was maintained at 35° C. and the fractions were collected manually, frozen at −70° C. and dried in a Speed Vac concentrator. Fragments were then solubilized in 20 mM sodium acetate, pH 4.0/0.5M NaCl prior to use.

Electrospray ionization mass spectrometry was performed on a VG Bio-Q mass spectrometer by Dr. Francis Bitsch and Mr. John Kim in the laboratory of Dr. Cedric Shackleton, Children's Hospital-Oakland Research Institute. Molecular masses were obtained by mathematical transformation of the data.

Figure 21A:
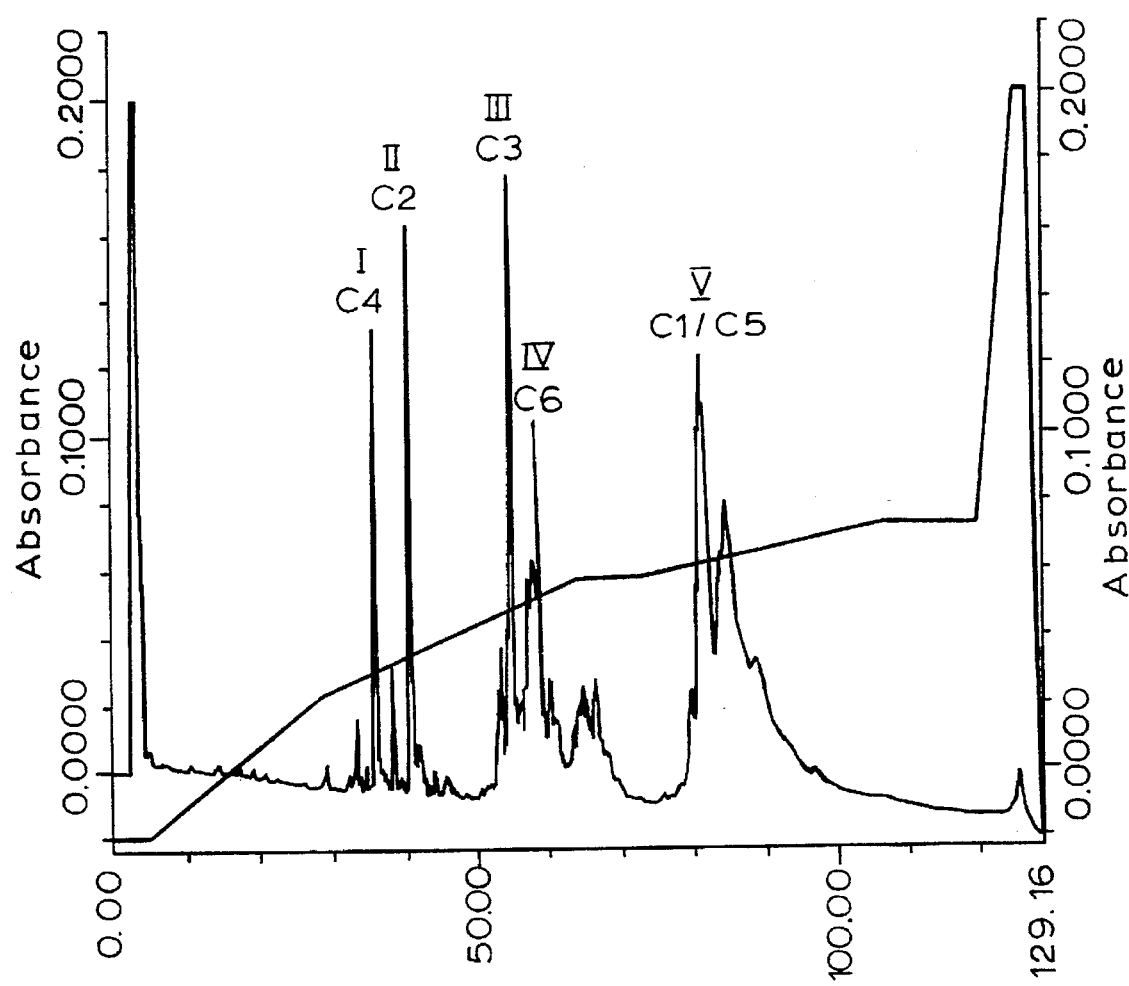
FIGS. 21a and 21b depict HPLC absorbance results for proteolytic fragments of $rBPI_{23}$.

Although the DNA sequence for rBPI$_{23}$ encodes amino acid residues 1–199 of the mature protein, a significant portion of the protein that is produced that is produced is truncated at Leu-193 and Val 195 as determined by electrospray ionization mass spectrometry (PSI-MS). These C-terminal truncations were verified by isolating the C-terminal tryptic peptides, which were sequenced and analyzed by ESI-MS. There are six methionine residues, at positions 56, 70, 100, 111, 170, and 196 and chemical cleavage by cyanogen bromide produced six major peptide fragments as predicted. The results of the CNBr cleavage experiments are summarized in Table 4. The fragments were isolated by reverse phase (C$_3$) HPLC (FIG. 21A) and their N-terminal sequences were determined by Edman degradation. The two largest fragments (C1 and C5) were not resolved by the C$_3$ HPLC column and further attempts to resolve them by ion exchange chromatography were unsuccessful, presumably because they are similar in length and isoelectric point. The identities of the C1, C5 fragments within the mixture were determined by PSI-MS. The predicted mass of C1 is 6269 (Table 4), taking into account the loss of 30 a.m.u. resulting from the conversion of the C-terminal methionine to homoserine during the CNBr cleavage reaction. The observed mass of 6251.51±0.34 is consistent with the loss of a water molecule (18 a.m.u.) in a homoserine lactone intermediate, which may be favored over the formation of the homoserine because of the hydrophobicity of the C 1 fragment C-terminal amino acids. The predicted mass of the C5 fragment is 6487 and the observed mass is 6385.84±0.39 (Table 1). For the C5 fragment, the C-terminal amino acids are hydrophilic, so the hydrolysis of the homoserine lactone intermediate is probably favored. From both the N-terminal sequencing and the mass spectrum dam, the C5 component represents approximately 10–25% of the material in the C1/C5 mixture.

Figure 21B:
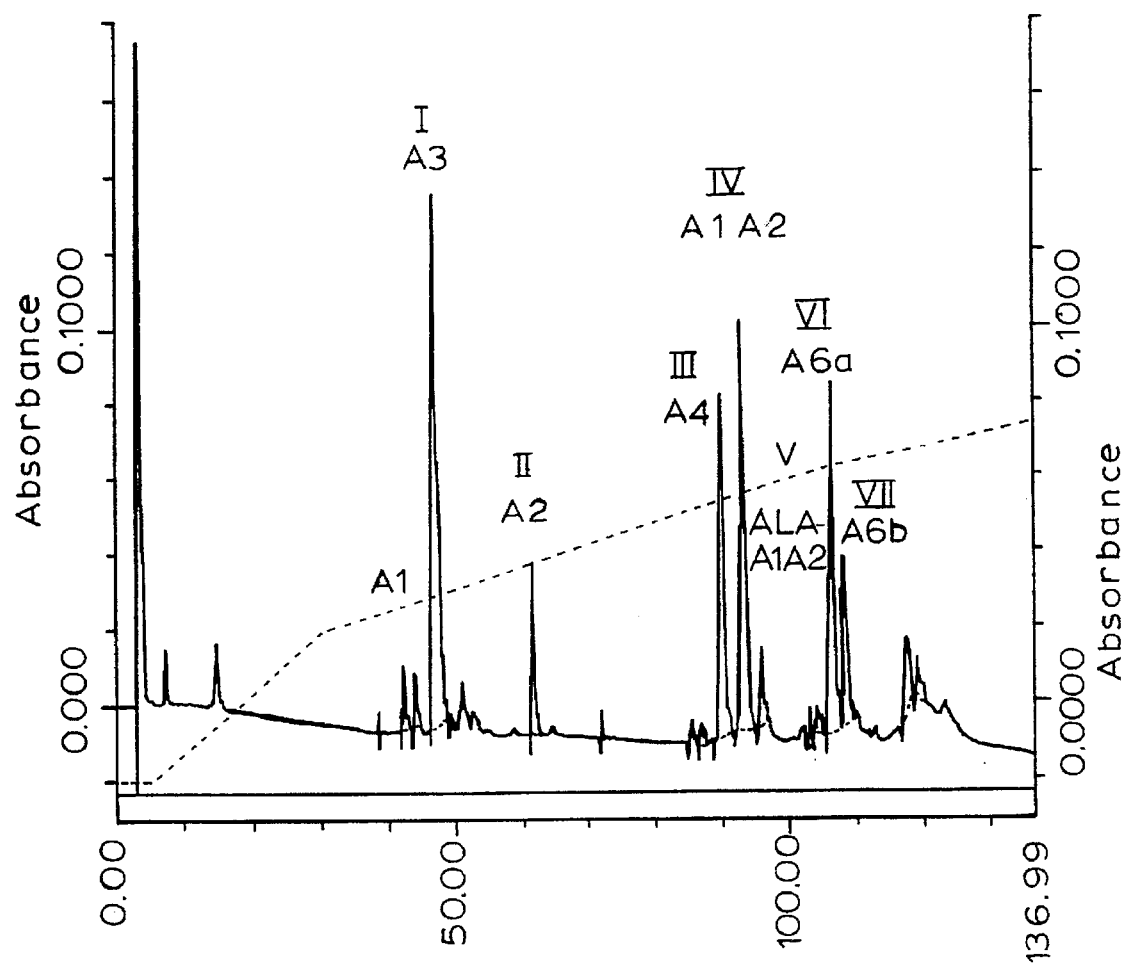

Proteolytic cleavage with endoproteinase Asp-N was performed to provide additional fragments for the regions contained within the CNBr C1/C5 mixture. There are six aspartic acid residues within the $rBPI_{23}$ sequence at positions 15, 36, 39, 57, 105, and 116. The six major Asp-N fragments isolated by $C_3$ HPLC (FIG. 21B) were sequenced and masses were determined by ESI-MS (Table 4). A short duration digest at a 1:1000 (w/w) enzyme:substrate ratio was used to eliminate potential non-specific cleavages, particularly at glutamic acid. It is evident that this digestion did not continue until completion, as one fragment (1–38) was isolated where Asp residues (amino acids 15 and 35) were not cleaved. The mass spectra of the Asp-N fragments were consistent with the predicted masses for each individual fragment. Unlike the CNBr cleavage, where the C-terminal fragment was poorly resolved, the Asp-N fragment from amino acid 116 to the C-terminus was well resolved from all of the other Asp-N fragments.

mutant *E. coli* J5 bacteria in a radial diffusion assay essentially according to the procedures of Example 16. No bactericidal activity was demonstrated for the $rBPI_{23}$ fragments generated by CNBr or by Asp-N digestion, when tested up to 25 pmol/well. This assay detected measurable bactericidal activity with as little as 0.75 pmol of $rBPI_{23}$ per well. Reduced and alkylated $rBPI_{23}$ (up to 100 pmol/well) also was not bactericidal, while alkylated $rBPI_{23}$ retained bactericidal activity equivalent to $rBPI_{23}$.

EXAMPLE 24

HEPARIN BINDING BY BPI PROTEOLYTIC FRAGMENTS $rBPI_{23}$ and BPI proteolytic fragments developed according to Example 22 were employed in heparin binding assays essentially according to the procedures of Example 1.

Heparin binding of CNBr fragments was estimated using 100 picomoles of each fragment per well with a saturating concentration of $^3$H-heparin (20 µg/ml). The results as shown in Table 5 (means of duplicate wells plus or minus the range between the two valves) indicate that the CNBr fragments containing the amino acids 71–100 (C3) and 1–56 and 112–170 (C1,5) bound heparin to a similar extent. The CNBr fragment 171–193 also bound more heparin than the control protein, thaumatin, a protein or similar molecular weight and charge to $rBPI_{23}$.

The Asp-N fragments also demonstrated multiple heparin binding regions in $rBPI_{23}$. As seen in Table 5, the 57–104 Asp-N fragment bound the highest amount of heparin, followed by the 1–38 and 116–193 fragments. These data, in combination with the CNBr fragment data, indicate that there are at least three separate heparin binding regions within $rBPI_{23}$, with the highest capacity residing within residues 71–100.

TABLE 4

SUMMARY OF $rBPI_{23}$ CLEAVAGE FRAGMENT ANALYSIS

| | | | MASS | |
|---|---|---|---|---|
| PEAK | SEQUENCE | I.D. | measured | predicted |
| CNBR Cleavage Fragments | | | | |
| I | 101–110 | C4(101–111) | Not Determined | 1169 |
| II | 57–67 | C2(57–70) | Not Determined | 1651 |
| II | 71–99 | C3(71–100) | Not Determined | 3404 |
| IV | 171–194 | C6(171–196) | Not Determined | 2929 |
| V | 1–25, 112–124 | C1(1–56), | 6251.51 ± 0.34 | 6299 |
| | | C5(112–170) | 6485.84 ± 0.39 | 6403 |
| Asp-N Proteolyic Fragments | | | | |
| A | 1–14 | A1(1–14) | 1465.5 | 1464 |
| I | 39–56 | A3(39–56) | 2145.2 | 2145 |
| II | 15–38 | A2(15–38) | 2723.6 | 2724 |
| III | 57–76 | A4(57–104) | 5442.5 | 5442 |
| IV | 1–38 | A1 A2(1–38) | 4171.4 | 4172 |
| VI | 116–134 | A6a(116–193) | 8800.3 | 8800 |
| VIII | 116–128 | A6b(116–195) | 8997.1 | 8996 |

EXAMPLE 23

BACTERICIDAL EFFECTS OF BPI PROTEOLYTIC FRAGMENTS

BPI proteolytic fragments developed according to Example 22 were screened for bactericidal effects rough

TABLE 5

| Heparin Binding of $rBPI_{23}$ Fragments | | |
|---|---|---|
| Fragments | Region | cpm $^3$H-Heparin bound |
| CNBr Digest | | |
| C1, C5 | 1–56, 112–170 | 82,918 ± 4,462 |
| C2 | 57–70 | 6,262 ± 182 |
| C3 | 71–100 | 81,655 ± 3,163 |
| C4 | 101–111 | 4,686 ± 4 |
| C6 | 171–196 | 26,204 ± 844 |
| Asp-N Digest | | |
| A1 | 1–38 | 17,002 ± 479 |
| A2 | 15–38 | 3,042 ± 162 |
| A3 | 39–56 | 8,664 ± 128 |
| A4 | 57–104 | 33,159 ± 1,095 |
| A6a | 116–193 | 13,419 ± 309 |
| $rBPI_{23}$ | 1–193 | 51,222 ± 1,808 |
| Thaumatin | | 7,432 ± 83 |
| Wash Buffer | | 6,366 ± 46 |

EXAMPLE 25

EFFECT OF BPI PROTEOLYTIC FRAGMENTS ON AN LAL ASSAY

Figure 22:
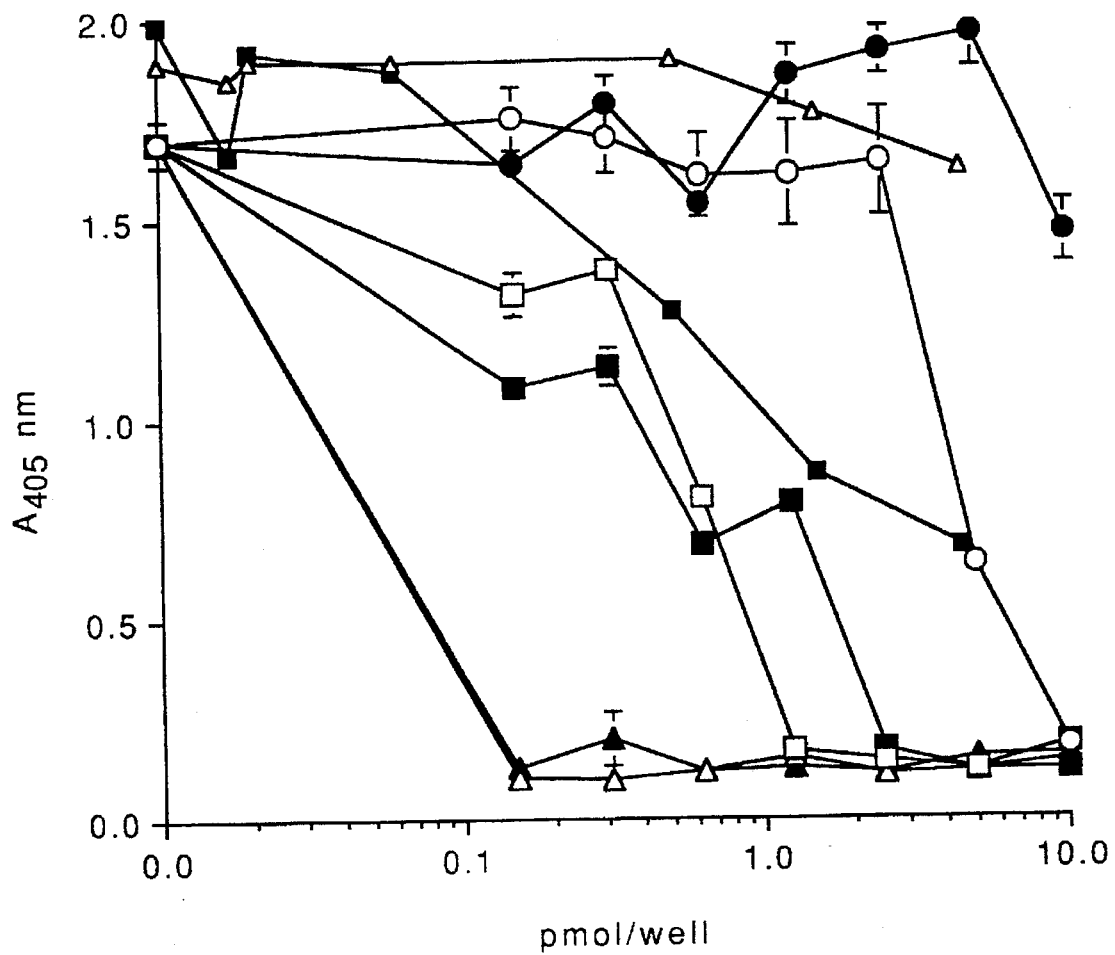
FIG. 22 depicts a graph of LAL inhibition assay results for proteolytic fragments of $rBPI_{23}$.

BPI proteolytic fragments developed according to Example 22 were employed in an LAL inhibition assay essentially as described in Example 15, providing results shown in FIG. 22 wherein: the filled triangle represents $rBPI_{23}$; the open circle represents Asp-N fragment A3; the closed circle represents Asp-N fragment A2; the open square represents Asp-N fragment A3; the filled square represents Asp-N fragment A1A2; the open triangle represents Asp-N fragment A6b; the small open triangle represents CNBr fragment C3; and the small filled square represents CNBr fragment C1/C5.

The CNBr digest fraction containing amino acid fragments 1–56 and 112–170 inhibited the LPS-induced LAL reaction with an $IC_{50}$ of approximately 100 nM. The $IC_{50}$ is approximately 10 fold higher than the $IC_{50}$ for $rBPI_{23}$ (9 nM) in the same assay. The other CNBr digest fragments were non-inhibitory.

A slightly different result was observed with fragments generated from the Asp-N digest, where three fragments were found to be inhibitory in the LAL assay. The fragment corresponding to amino acids 116–193 exhibited LAL inhibitory activity similar to intact $rBPI_{23}$ with complete inhibition of the LPS-induced LAL reaction at 15 nM. The fragments corresponding to amino acids 57–104 and 1–38 also inhibited the LAL assay, but required 10 fold higher amounts. These results, in combination with the CNBr digest results, indicate that at least three regions of the $rBPI_{23}$ molecule have the ability to neutralize LBS activation of the LAL reaction with the most potent region appearing to exist within the 116–193 amino acid fragment.

In related studies of the proteolytic fragments of Example 22 involving ELISA assays using a rabbit polyclonal anti-$rBPI_{23}$ antibody capable of blocking $rBPI_{23}$ bactericidal and LAL inhibition properties and two different, non-blocking mouse anti-$rBPI_{23}$ monoclonal antibodies, the polyclonal antibody was noted to be immunoreactive with the 116–193 and 57–104 Asp-N fragments as well as the 1–56 and 112–170 CNBr fragments while the murine monoclonal antibodies reacted only with an Asp-N fragment representing residues 1–14 of $rBPI_{23}$.

Overall, the results indicate that $rBPI_{23}$ contains three functional domains that contribute to the total biological activity of the molecule. The first domain appears in the sequence of amino acids 17–45 and is destroyed by Asp-N cleavage at residue 36. This domain is moderately active in both the inhibition of LPS-induced LAL activity and heparin binding assays. The second active domain appears in the region of amino acids 65–99 and its inhibition of LPS-induced LAL activity is diminished by CNBr cleavage at residue 70. This domain also exhibits the highest heparin binding capacity and contains the bactericidal peptide, 85–99. The third active domain, between amino acids 142–169, is active in the inhibition of LPS-induced LAL stimulation assay and exhibits the lowest heparin binding capacity of the three regions.

Figure 15:
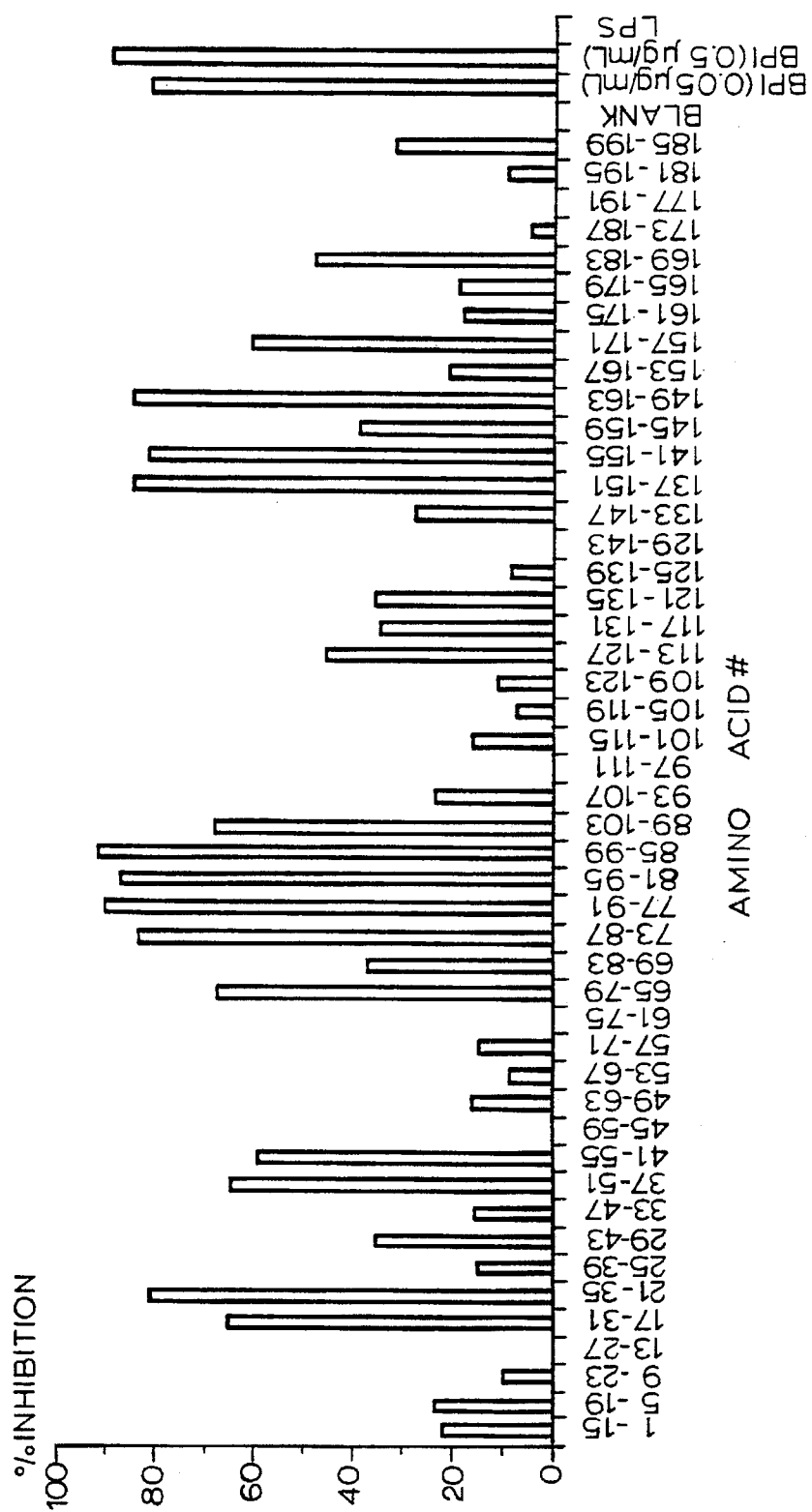
FIG. 15 depicts a graph of a Limulus Amoebocyte Lysate (LAL) inhibition assay for synthetic BPI peptides.

Other bactericidal proteins, for example, cecropins and magainins, are characterized by a continuous, amphipathic, α-helical region which is necessary for activity. A high degree of structural similarity was observed between the cationic/hydrophobic motif of LPS binding/bactericidal molecules and the consensus sequences of heparin binding proteins. An excellent correlation exists between the synthetic $rBPI_{23}$ peptides that bind to heparin and those which inhibit the LPS-induced LAL reaction (r=0.75, p=0.0001, n=47) (FIGS. 14 through 16). These data suggest that LPS and heparin may present similar charged arrays to the proteins with which they interact. As a result, other proteins which bind to LPS avidly, may also bind tightly to heparin.

Numerous modifications and variations in the practice of the invention are expected to occur to those skilled in the art upon consideration of the presently preferred embodiments thereof. According to one aspect of the invention, methods of treating gram-negative bacterial infections and the sequelae thereof are contemplated which comprise administration of BPI protein product peptides having gram-negative bactericidal activity. Consequently, the only limitations which should be placed upon the scope of the invention are those which appear in the appended claims.

What is claimed is:

1. A method for treating a chronic inflammatory disease state comprising administering to a subject suffering from a chronic inflammatory disease state an amount of a bactericidal/permeability-increasing (BPI) protein product effective to reduce inflammation.

2. The method of claim 1 wherein the chronic inflammatory disease state is an arthritic inflammatory disease state.

3. The method of claim 2 wherein the arthritic inflammatory disease state is rheumatoid arthritis.

4. The method of claim 2 wherein the arthritic inflammatory disease state treated is reactive arthritis.

5. The method of any one of claims 1, 2, 3 and 4 wherein the BPI protein product is an amino-terminal fragment of bactericidal/permeability-increasing protein having an approximate molecular weight of between 21 and 25 kD.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1813 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 31..1491

( i x ) FEATURE:
        ( A ) NAME/KEY: mat_peptide
        ( B ) LOCATION: 124..1491

( x i ) SEQUENCE DESCRIPTION: SEQ ID NO:1:

```
CAGGCCTTGA  GGTTTTGGCA  GCTCTGGAGG  ATG  AGA  GAG  AAC  ATG  GCC  AGG  GGC        54
                                    Met  Arg  Glu  Asn  Met  Ala  Arg  Gly
                                    -31  -30                           -25
```

| | | | | | | | | | | | | | | | | |
|---|---|---|---|---|---|---|---|---|---|---|---|---|---|---|---|---|
| CCT | TGC | AAC | GCG | CCG | AGA | TGG | GTG | TCC | CTG | ATG | GTG | CTC | GTC | GCC | ATA | 102 |
| Pro | Cys | Asn | Ala<br>-20 | Pro | Arg | Trp | Val | Ser<br>-15 | Leu | Met | Val | Leu | Val | Ala<br>-10 | Ile | |
| GGC | ACC | GCC | GTG | ACA | GCG | GCC | GTC | AAC | CCT | GGC | GTC | GTG | GTC | AGG | ATC | 150 |
| Gly | Thr | Ala | Val<br>-5 | Thr | Ala | Ala | Val | Asn<br>1 | Pro | Gly | Val | Val<br>5 | Val | Arg | Ile | |
| TCC | CAG | AAG | GGC | CTG | GAC | TAC | GCC | AGC | CAG | CAG | GGG | ACG | GCC | GCT | CTG | 198 |
| Ser<br>10 | Gln | Lys | Gly | Leu | Asp<br>15 | Tyr | Ala | Ser | Gln | Gln<br>20 | Gly | Thr | Ala | Ala | Leu<br>25 | |
| CAG | AAG | GAG | CTG | AAG | AGG | ATC | AAG | ATT | CCT | GAC | TAC | TCA | GAC | AGC | TTT | 246 |
| Gln | Lys | Glu | Leu | Lys<br>30 | Arg | Ile | Lys | Ile | Pro<br>35 | Asp | Tyr | Ser | Asp | Ser<br>40 | Phe | |
| AAG | ATC | AAG | CAT | CTT | GGG | AAG | GGG | CAT | TAT | AGC | TTC | TAC | AGC | ATG | GAC | 294 |
| Lys | Ile | Lys | His<br>45 | Leu | Gly | Lys | Gly | His<br>50 | Tyr | Ser | Phe | Tyr | Ser<br>55 | Met | Asp | |
| ATC | CGT | GAA | TTC | CAG | CTT | CCC | AGT | TCC | CAG | ATA | AGC | ATG | GTG | CCC | AAT | 342 |
| Ile | Arg | Glu<br>60 | Phe | Gln | Leu | Pro | Ser<br>65 | Ser | Gln | Ile | Ser | Met<br>70 | Val | Pro | Asn | |
| GTG | GGC | CTT | AAG | TTC | TCC | ATC | AGC | AAC | GCC | AAT | ATC | AAG | ATC | AGC | GGG | 390 |
| Val | Gly<br>75 | Leu | Lys | Phe | Ser | Ile<br>80 | Ser | Asn | Ala | Asn | Ile<br>85 | Lys | Ile | Ser | Gly | |
| AAA | TGG | AAG | GCA | CAA | AAG | AGA | TTC | TTA | AAA | ATG | AGC | GGC | AAT | TTT | GAC | 438 |
| Lys<br>90 | Trp | Lys | Ala | Gln | Lys<br>95 | Arg | Phe | Leu | Lys | Met<br>100 | Ser | Gly | Asn | Phe | Asp<br>105 | |
| CTG | AGC | ATA | GAA | GGC | ATG | TCC | ATT | TCG | GCT | GAT | CTG | AAG | CTG | GGC | AGT | 486 |
| Leu | Ser | Ile | Glu | Gly<br>110 | Met | Ser | Ile | Ser | Ala<br>115 | Asp | Leu | Lys | Leu | Gly<br>120 | Ser | |
| AAC | CCC | ACG | TCA | GGC | AAG | CCC | ACC | ATC | ACC | TGC | TCC | AGC | TGC | AGC | AGC | 534 |
| Asn | Pro | Thr | Ser<br>125 | Gly | Lys | Pro | Thr | Ile<br>130 | Thr | Cys | Ser | Ser | Cys<br>135 | Ser | Ser | |
| CAC | ATC | AAC | AGT | GTC | CAC | GTG | CAC | ATC | TCA | AAG | AGC | AAA | GTC | GGG | TGG | 582 |
| His | Ile | Asn<br>140 | Ser | Val | His | Val | His<br>145 | Ile | Ser | Lys | Ser | Lys<br>150 | Val | Gly | Trp | |
| CTG | ATC | CAA | CTC | TTC | CAC | AAA | AAA | ATT | GAG | TCT | GCG | CTT | CGA | AAC | AAG | 630 |
| Leu | Ile<br>155 | Gln | Leu | Phe | His | Lys<br>160 | Lys | Ile | Glu | Ser | Ala<br>165 | Leu | Arg | Asn | Lys | |
| ATG | AAC | AGC | CAG | GTC | TGC | GAG | AAA | GTG | ACC | AAT | TCT | GTA | TCC | TCC | AAG | 678 |
| Met<br>170 | Asn | Ser | Gln | Val | Cys<br>175 | Glu | Lys | Val | Thr | Asn<br>180 | Ser | Val | Ser | Ser | Lys<br>185 | |
| CTG | CAA | CCT | TAT | TTC | CAG | ACT | CTG | CCA | GTA | ATG | ACC | AAA | ATA | GAT | TCT | 726 |
| Leu | Gln | Pro | Tyr | Phe<br>190 | Gln | Thr | Leu | Pro | Val<br>195 | Met | Thr | Lys | Ile | Asp<br>200 | Ser | |
| GTG | GCT | GGA | ATC | AAC | TAT | GGT | CTG | GTG | GCA | CCT | CCA | GCA | ACC | ACG | GCT | 774 |
| Val | Ala | Gly | Ile<br>205 | Asn | Tyr | Gly | Leu | Val<br>210 | Ala | Pro | Pro | Ala | Thr<br>215 | Thr | Ala | |
| GAG | ACC | CTG | GAT | GTA | CAG | ATG | AAG | GGG | GAG | TTT | TAC | AGT | GAG | AAC | CAC | 822 |
| Glu | Thr | Leu<br>220 | Asp | Val | Gln | Met | Lys<br>225 | Gly | Glu | Phe | Tyr | Ser<br>230 | Glu | Asn | His | |
| CAC | AAT | CCA | CCT | CCC | TTT | GCT | CCA | CCA | GTG | ATG | GAG | TTT | CCC | GCT | GCC | 870 |
| His | Asn<br>235 | Pro | Pro | Pro | Phe | Ala<br>240 | Pro | Pro | Val | Met<br>245 | Glu | Phe | Pro | Ala | Ala | |
| CAT | GAC | CGC | ATG | GTA | TAC | CTG | GGC | CTC | TCA | GAC | TAC | TTC | TTC | AAC | ACA | 918 |
| His<br>250 | Asp | Arg | Met | Val | Tyr<br>255 | Leu | Gly | Leu | Ser | Asp<br>260 | Tyr | Phe | Phe | Asn | Thr<br>265 | |
| GCC | GGG | CTT | GTA | TAC | CAA | GAG | GCT | GGG | GTC | TTG | AAG | ATG | ACC | CTT | AGA | 966 |
| Ala | Gly | Leu | Val | Tyr<br>270 | Gln | Glu | Ala | Gly | Val<br>275 | Leu | Lys | Met | Thr | Leu<br>280 | Arg | |
| GAT | GAC | ATG | ATT | CCA | AAG | GAG | TCC | AAA | TTT | CGA | CTG | ACA | ACC | AAG | TTC | 1014 |
| Asp | Asp | Met | Ile<br>285 | Pro | Lys | Glu | Ser | Lys<br>290 | Phe | Arg | Leu | Thr | Thr<br>295 | Lys | Phe | |

-continued

```
TTT  GGA  ACC  TTC  CTA  CCT  GAG  GTG  GCC  AAG  AAG  TTT  CCC  AAC  ATG  AAG    1062
Phe  Gly  Thr  Phe  Leu  Pro  Glu  Val  Ala  Lys  Lys  Phe  Pro  Asn  Met  Lys
          300                 305                      310

ATA  CAG  ATC  CAT  GTC  TCA  GCC  TCC  ACC  CCG  CCA  CAC  CTG  TCT  GTG  CAG    1110
Ile  Gln  Ile  His  Val  Ser  Ala  Ser  Thr  Pro  Pro  His  Leu  Ser  Val  Gln
     315                      320                      325

CCC  ACC  GGC  CTT  ACC  TTC  TAC  CCT  GCC  GTG  GAT  GTC  CAG  GCC  TTT  GCC    1158
Pro  Thr  Gly  Leu  Thr  Phe  Tyr  Pro  Ala  Val  Asp  Val  Gln  Ala  Phe  Ala
330                 335                      340                      345

GTC  CTC  CCC  AAC  TCC  TCC  CTG  GCT  TCC  CTC  TTC  CTG  ATT  GGC  ATG  CAC    1206
Val  Leu  Pro  Asn  Ser  Ser  Leu  Ala  Ser  Leu  Phe  Leu  Ile  Gly  Met  His
               350                 355                      360

ACA  ACT  GGT  TCC  ATG  GAG  GTC  AGC  GCC  GAG  TCC  AAC  AGG  CTT  GTT  GGA    1254
Thr  Thr  Gly  Ser  Met  Glu  Val  Ser  Ala  Glu  Ser  Asn  Arg  Leu  Val  Gly
          365                 370                      375

GAG  CTC  AAG  CTG  GAT  AGG  CTG  CTC  GAA  CTG  AAG  CAC  TCA  AAT  ATT         1302
Glu  Leu  Lys  Leu  Asp  Arg  Leu  Leu  Glu  Leu  Lys  His  Ser  Asn  Ile
          380                 385                      390

GGC  CCC  TTC  CCG  GTT  GAA  TTG  CTG  CAG  GAT  ATC  ATG  AAC  TAC  ATT  GTA    1350
Gly  Pro  Phe  Pro  Val  Glu  Leu  Leu  Gln  Asp  Ile  Met  Asn  Tyr  Ile  Val
     395                      400                      405

CCC  ATT  CTT  GTG  CTG  CCC  AGG  GTT  AAC  GAG  AAA  CTA  CAG  AAA  GGC  TTC    1398
Pro  Ile  Leu  Val  Leu  Pro  Arg  Val  Asn  Glu  Lys  Leu  Gln  Lys  Gly  Phe
410                      415                      420                      425

CCT  CTC  CCG  ACG  CCG  GCC  AGA  GTC  CAG  CTC  TAC  AAC  GTA  GTG  CTT  CAG    1446
Pro  Leu  Pro  Thr  Pro  Ala  Arg  Val  Gln  Leu  Tyr  Asn  Val  Val  Leu  Gln
               430                 435                      440

CCT  CAC  CAG  AAC  TTC  CTG  CTG  TTC  GGT  GCA  GAC  GTT  GTC  TAT  AAA         1491
Pro  His  Gln  Asn  Phe  Leu  Leu  Phe  Gly  Ala  Asp  Val  Val  Tyr  Lys
               445                 450                      455

TGAAGGCACC  AGGGGTGCCG  GGGGCTGTCA  GCCGCACCTG  TTCCTGATGG  GCTGTGGGGC            1551

ACCGGCTGCC  TTTCCCCAGG  GAATCCTCTC  CAGATCTTAA  CCAAGAGCCC  CTTGCAAACT            1611

TCTTCGACTC  AGATTCAGAA  ATGATCTAAA  CACGAGGAAA  CATTATTCAT  TGGAAAAGTG            1671

CATGGTGTGT  ATTTTAGGGA  TTATGAGCTT  CTTTCAAGGG  CTAAGGCTGC  AGAGATATTT            1731

CCTCCAGGAA  TCGTGTTTCA  ATTGTAACCA  AGAAATTTCC  ATTTGTGCTT  CATGAAAAAA            1791

AACTTCTGGT  TTTTTCATG  TG                                                         1813
```

( 2 ) INFORMATION FOR SEQ ID NO:2:

( i ) SEQUENCE CHARACTERISTICS:
        ( A ) LENGTH: 487 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Arg  Glu  Asn  Met  Ala  Arg  Gly  Pro  Cys  Asn  Ala  Pro  Arg  Trp  Val
-31  -30                 -25                 -20

Ser  Leu  Met  Val  Leu  Val  Ala  Ile  Gly  Thr  Ala  Val  Thr  Ala  Ala  Val
-15                      -10                 -5                            1

Asn  Pro  Gly  Val  Val  Val  Arg  Ile  Ser  Gln  Lys  Gly  Leu  Asp  Tyr  Ala
               5                    10                      15

Ser  Gln  Gln  Gly  Thr  Ala  Ala  Leu  Gln  Lys  Glu  Leu  Lys  Arg  Ile  Lys
          20                      25                      30

Ile  Pro  Asp  Tyr  Ser  Asp  Ser  Phe  Lys  Ile  Lys  His  Leu  Gly  Lys  Gly
          35                      40                      45
```

| | | | | | | | | | | | | | | |
|---|---|---|---|---|---|---|---|---|---|---|---|---|---|---|
| His | Tyr | Ser | Phe | Tyr | Ser | Met | Asp | Ile | Arg | Glu | Phe | Gln | Leu | Pro | Ser |
| 50 | | | | | 55 | | | | | 60 | | | | | 65 |
| Ser | Gln | Ile | Ser | Met | Val | Pro | Asn | Val | Gly | Leu | Lys | Phe | Ser | Ile | Ser |
| | | | | 70 | | | | | 75 | | | | | 80 | |
| Asn | Ala | Asn | Ile | Lys | Ile | Ser | Gly | Lys | Trp | Lys | Ala | Gln | Lys | Arg | Phe |
| | | | | 85 | | | | | 90 | | | | | 95 | |
| Leu | Lys | Met | Ser | Gly | Asn | Phe | Asp | Leu | Ser | Ile | Glu | Gly | Met | Ser | Ile |
| | | | 100 | | | | | 105 | | | | | 110 | | |
| Ser | Ala | Asp | Leu | Lys | Leu | Gly | Ser | Asn | Pro | Thr | Ser | Gly | Lys | Pro | Thr |
| | | | 115 | | | | | 120 | | | | | 125 | | |
| Ile | Thr | Cys | Ser | Ser | Cys | Ser | Ser | His | Ile | Asn | Ser | Val | His | Val | His |
| 130 | | | | | 135 | | | | | 140 | | | | | 145 |
| Ile | Ser | Lys | Ser | Lys | Val | Gly | Trp | Leu | Ile | Gln | Leu | Phe | His | Lys | Lys |
| | | | | 150 | | | | | 155 | | | | | 160 | |
| Ile | Glu | Ser | Ala | Leu | Arg | Asn | Lys | Met | Asn | Ser | Gln | Val | Cys | Glu | Lys |
| | | | | 165 | | | | | 170 | | | | | 175 | |
| Val | Thr | Asn | Ser | Val | Ser | Ser | Lys | Leu | Gln | Pro | Tyr | Phe | Gln | Thr | Leu |
| | | | 180 | | | | | 185 | | | | | 190 | | |
| Pro | Val | Met | Thr | Lys | Ile | Asp | Ser | Val | Ala | Gly | Ile | Asn | Tyr | Gly | Leu |
| | | | 195 | | | | | 200 | | | | | 205 | | |
| Val | Ala | Pro | Pro | Ala | Thr | Thr | Ala | Glu | Thr | Leu | Asp | Val | Gln | Met | Lys |
| 210 | | | | | 215 | | | | | 220 | | | | | 225 |
| Gly | Glu | Phe | Tyr | Ser | Glu | Asn | His | His | Asn | Pro | Pro | Phe | Ala | Pro | |
| | | | | 230 | | | | | 235 | | | | | 240 | |
| Pro | Val | Met | Glu | Phe | Pro | Ala | Ala | His | Asp | Arg | Met | Val | Tyr | Leu | Gly |
| | | | | 245 | | | | | 250 | | | | | 255 | |
| Leu | Ser | Asp | Tyr | Phe | Phe | Asn | Thr | Ala | Gly | Leu | Val | Tyr | Gln | Glu | Ala |
| | | | 260 | | | | | 265 | | | | | 270 | | |
| Gly | Val | Leu | Lys | Met | Thr | Leu | Arg | Asp | Asp | Met | Ile | Pro | Lys | Glu | Ser |
| | | | 275 | | | | | 280 | | | | | 285 | | |
| Lys | Phe | Arg | Leu | Thr | Thr | Lys | Phe | Phe | Gly | Thr | Phe | Leu | Pro | Glu | Val |
| 290 | | | | | 295 | | | | | 300 | | | | | 305 |
| Ala | Lys | Lys | Phe | Pro | Asn | Met | Lys | Ile | Gln | Ile | His | Val | Ser | Ala | Ser |
| | | | | 310 | | | | | 315 | | | | | 320 | |
| Thr | Pro | Pro | His | Leu | Ser | Val | Gln | Pro | Thr | Gly | Leu | Thr | Phe | Tyr | Pro |
| | | | 325 | | | | | 330 | | | | | 335 | | |
| Ala | Val | Asp | Val | Gln | Ala | Phe | Ala | Val | Leu | Pro | Asn | Ser | Ser | Leu | Ala |
| | | | 340 | | | | | 345 | | | | | 350 | | |
| Ser | Leu | Phe | Leu | Ile | Gly | Met | His | Thr | Thr | Gly | Ser | Met | Glu | Val | Ser |
| | 355 | | | | | 360 | | | | | 365 | | | | |
| Ala | Glu | Ser | Asn | Arg | Leu | Val | Gly | Glu | Leu | Lys | Leu | Asp | Arg | Leu | Leu |
| 370 | | | | | 375 | | | | | 380 | | | | | 385 |
| Leu | Glu | Leu | Lys | His | Ser | Asn | Ile | Gly | Pro | Phe | Pro | Val | Glu | Leu | Leu |
| | | | | 390 | | | | | 395 | | | | | 400 | |
| Gln | Asp | Ile | Met | Asn | Tyr | Ile | Val | Pro | Ile | Leu | Val | Leu | Pro | Arg | Val |
| | | | | 405 | | | | | 410 | | | | | 415 | |
| Asn | Glu | Lys | Leu | Gln | Lys | Gly | Phe | Pro | Leu | Pro | Thr | Pro | Ala | Arg | Val |
| | | | | 420 | | | | | 425 | | | | | 430 | |
| Gln | Leu | Tyr | Asn | Val | Val | Leu | Gln | Pro | His | Gln | Asn | Phe | Leu | Leu | Phe |
| | | | 435 | | | | | 440 | | | | | 445 | | |
| Gly | Ala | Asp | Val | Val | Tyr | Lys | | | | | | | | | |
| 450 | | | | | 455 | | | | | | | | | | |